(12) United States Patent
Kojima

(10) Patent No.: US 11,668,285 B2
(45) Date of Patent: Jun. 6, 2023

(54) METHOD FOR DIAGNOSING LUBRICANT AND SYSTEM OF MONITORING LUBRICANT

(71) Applicant: HITACHI, LTD., Tokyo (JP)

(72) Inventor: Kyoko Kojima, Tokyo (JP)

(73) Assignee: HITACHI, LTD., Tokyo (JP)

( * ) Notice: Subject to any disclaimer, the term of this patent is extended or adjusted under 35 U.S.C. 154(b) by 229 days.

(21) Appl. No.: 16/827,848

(22) Filed: Mar. 24, 2020

(65) Prior Publication Data
US 2020/0355163 A1  Nov. 12, 2020

(30) Foreign Application Priority Data

May 10, 2019 (JP) .............................. JP2019-089854

(51) Int. Cl.
*F03D 17/00* (2016.01)
*G01N 33/28* (2006.01)
(Continued)

(52) U.S. Cl.
CPC ......... *F03D 17/00* (2016.05); *G01N 33/2888* (2013.01); *F03D 80/70* (2016.05);
(Continued)

(58) Field of Classification Search
CPC ............. F05B 2260/98; F05B 2260/80; G05B 23/0283; G01N 33/2888
(Continued)

(56) References Cited

U.S. PATENT DOCUMENTS

| 2010/0134286 A1 | 6/2010 | Potyrailo et al. | |
| 2012/0086942 A1* | 4/2012 | Honda ................... | G01N 21/31 356/436 |

(Continued)

FOREIGN PATENT DOCUMENTS

| JP | 2012-117951 A | 6/2012 |
| JP | 2012-181168 A | 9/2012 |

(Continued)

OTHER PUBLICATIONS

Japanese Office Action dated Aug. 30, 2022 for Japanese Patent Application No. 2019-089854.
(Continued)

*Primary Examiner* — Ricky Go
(74) *Attorney, Agent, or Firm* — Volpe Koenig

(57) ABSTRACT

A method for diagnosing a lubricant containing an additive, is executed by an information processor. Chromaticity information of the lubricant which is a diagnosis target is obtained from an input device, the chromaticity information is obtained by an optical sensor, and a storage device stores a deterioration curve of the lubricant which is the diagnosis target, the deterioration curve is determined in advance regarding a transition in a chromaticity coordinate caused by a deterioration, and a chromaticity coordinate corresponding to a limit contamination level determined in advance using a contaminated lubricant. The processing device obtains a chromaticity coordinate of the lubricant from the chromaticity information and uses a relative contamination level obtained from a distance of the chromaticity coordinate of the lubricant from the deterioration curve and a distance of the chromaticity coordinate corresponding to the limit contamination level from the deterioration curve.

12 Claims, 16 Drawing Sheets

(51) Int. Cl.
*F03D 80/70* (2016.01)
*G05B 23/02* (2006.01)

(52) U.S. Cl.
CPC ....... *F05B 2260/80* (2013.01); *F05B 2270/32* (2013.01); *F05B 2270/334* (2013.01); *F16C 2360/31* (2013.01); *F16N 2250/08* (2013.01); *G05B 23/0283* (2013.01)

(58) Field of Classification Search
USPC .......................................................... 702/183
See application file for complete search history.

(56) References Cited

U.S. PATENT DOCUMENTS

| | | | | |
|---|---|---|---|---|
| 2013/0250303 | A1* | 9/2013 | Shi | B25J 13/087 |
| | | | | 356/436 |
| 2014/0007657 | A1 | 1/2014 | Matsubara et al. | |
| 2016/0054288 | A1 | 2/2016 | O Donnell | |
| 2016/0161463 | A1* | 6/2016 | Onuma | G01N 21/27 |
| | | | | 356/70 |
| 2016/0252448 | A1* | 9/2016 | Ida | G01N 21/8507 |
| | | | | 356/70 |
| 2016/0252490 | A1* | 9/2016 | Shi | G01N 21/255 |
| | | | | 356/70 |
| 2018/0003618 | A1* | 1/2018 | Shinoda | G01N 21/251 |

FOREIGN PATENT DOCUMENTS

| | | |
|---|---|---|
| JP | 2016-044681 A | 4/2016 |
| JP | 2016-126007 A | 7/2016 |
| JP | 2018-194011 A | 12/2018 |
| WO | 2010/150526 A1 | 12/2010 |
| WO | 2016/114302 A1 | 7/2016 |

OTHER PUBLICATIONS

"Chromaticity coordinates", subparagraph, The Britannica International Large Encyclopedia (with English concise explanation of the relevance) (2016).

* cited by examiner

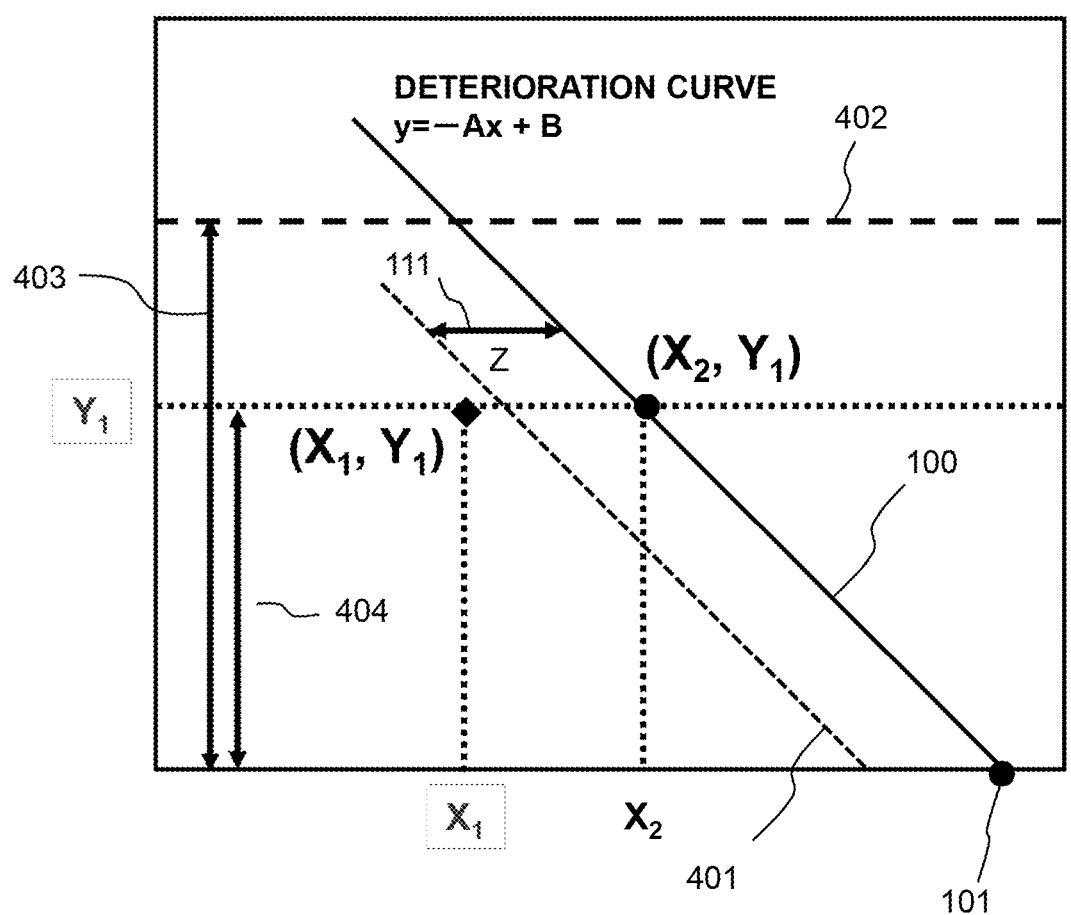

METHOD FOR DIAGNOSING LUBRICANT AND SYSTEM OF MONITORING LUBRICANT

BACKGROUND OF THE INVENTION

1. Field of the Invention

The present invention relates to a technique of diagnosing a lubricant, particularly to a technique of diagnosing a lubricant that is used in a rotary machine such as a wind power generator.

2. Description of the Related Art

The diagnosis of the properties of a lubricant is an important technique in the preservation and the maintenance of a rotary machine. Examples of a change in the properties of the lubricant include a change caused by the oxidation of a base oil, a change caused by contaminants, a change caused by the mixing in of moisture, and a change in an additive. In the related art, the diagnoses of the lubricant are disclosed in, for example, JP 2016-126007 A, WO 2010/150526 A, JP 2012-117951 A, JP 2012-181168 A, and JP 2016-044681 A. JP 2016-126007 A discloses a system that measures a resonant impedance spectral response of an LC resonator to detect water, soot, and friction products contained in a fluid.

WO 2010/150526 A discloses a method where the state of a lubricant is monitored by filtering the lubricant or the like used in various machines or facilities using a filter, removing oil from the filter that traps contaminants, projecting light onto the filter from which the oil is removed, and detecting the color components of transmitted light that is transmitted through the filter from which the oil is removed.

JP 2012-117951 A discloses a method for specifying the types of contaminants in a lubricant based on colors detected by an optical sensor.

JP 2012-181168 A discloses a method for monitoring the concentration of mixed moisture in a lubricant by capacitance detection means.

JP 2016-044681 A discloses a method where a lubricant from a wind turbine is monitored by determining an initial ideal residual life of the lubricant from the wind turbine, determining a temperature-based residual life of the lubricant based on a temperature measurement value of the lubricant from the wind turbine, calculating a contamination factor of the lubricant based on a contamination sample of the lubricant, determining an updated ideal residual life of the lubricant based on the contamination factor, the initial ideal residual life, and the temperature-based residual life, and determining an actual residual life of the lubricant based on the updated ideal residual life and a life loss factor. The contamination factor based on the contamination sample is calculated based on the properties (at least one measurement value of an iron particle count, a water content, a dielectric constant, and an International Organization for Standardization (ISO)-level particle count) of the lubricant.

In addition, WO 2016/114302 A describes methods where a lubricant is determined from an antioxidant content in the lubricant or the lubricant is determined from a color difference in the lubricant.

The monitoring of the contamination and the deterioration of a lubricant which is used in a rotary machine such as a gearbox of a wind turbine is a very important technique. The reason is that due to an abnormality of the lubricant occurring earlier than other sensing means for sensing vibration, temperature, noise, and the like, an abnormality of the machine can be found. It is known that the contamination of the lubricant by solid particles or the mixing of water into the lubricant significantly decreases the life of an important machine component such as bearings or gears. In addition, it is known that when the amount of an additive such as an extreme-pressure agent or an anti-wear agent is reduced since the lubricant chemically deteriorates over time as the lubricant is used, the wear of the machine easily occurs.

It is possible to monitor the state of the lubricant by measuring the chromaticity of the lubricant using a sensor; however, even when the measured chromaticity is simply displayed, since the contamination level or a residual life of the lubricant is not known, it is necessary to quantitatively indicate the contamination and the deterioration of the lubricant.

SUMMARY OF THE INVENTION

An object of the present invention is to provide a technique of diagnosing a lubricant, in which the contamination and the deterioration of the lubricant can be quantitatively diagnosed.

According to one preferred aspect of the present invention, there is provided a method for diagnosing a lubricant containing an additive, which is executed by an information processing apparatus including an input device, a processing device, a storage device, and an output device, the method including a diagnosis of a deterioration, and a diagnosis of a contamination. Chromaticity information of the lubricant which is a diagnosis target is obtained from the input device, the chromaticity information being obtained by an optical sensor, and the storage device stores a deterioration curve of the lubricant which is the diagnosis target, the deterioration curve being determined in advance regarding a transition in a chromaticity coordinate caused by a deterioration, and a chromaticity coordinate corresponding to a limit contamination level determined in advance using a contaminated lubricant. In the diagnosis of the contamination of the lubricant, the processing device obtains a chromaticity coordinate of the lubricant, which is the diagnosis target, from the chromaticity information, and uses a relative contamination level which is obtained from a distance of the chromaticity coordinate of the lubricant, which is the diagnosis target, from the deterioration curve and a distance of the chromaticity coordinate corresponding to the limit contamination level from the deterioration curve.

In a more specific example of the present invention, in the diagnosis of the deterioration of the lubricant, a concentration of the additive contained in the lubricant which is the diagnosis target is quantified based on the chromaticity coordinate of the lubricant which is the diagnosis target, and a correlation obtained in advance. Alternatively, in the diagnosis of the deterioration of the lubricant, a chromaticity coordinate of a limit deterioration level is determined in advance with respect to the deterioration curve, and a relative deterioration level, which is obtained from the chromaticity coordinate of the lubricant which is the diagnosis target and the chromaticity coordinate of the limit deterioration level, is used. In addition, in a preferred example, the diagnosis of the contamination is performed before the diagnosis of the deterioration.

According to another preferred aspect of the present invention, there is provided a system of monitoring a lubricant that is supplied to a drive unit of a rotary machine. The system includes an optical sensor that measures data regarding a chromaticity of the lubricant, an input device, a processing device, a storage device, and an output device. The processing device quantifies a contamination level and a deterioration level of the lubricant which is a monitoring target based on a relationship, which is obtained in advance, between a concentration of an additive contained in a lubricant having a different degree of deterioration and a chromaticity coordinate of the lubricant having the different degree of deterioration, the chromaticity coordinate being obtained by the optical sensor, and a deterioration curve of the lubricant which is the monitoring target.

In a more preferred specific example, the storage device holds data of the deterioration curve which indicates a transition in the chromaticity of the lubricant on a chromaticity coordinate as the lubricant deteriorates. In addition, the storage device holds data of a contamination level threshold curve which indicates a threshold value for a contamination level of the lubricant on the chromaticity coordinate by the chromaticity of the lubricant. The processing device calculates a relative contamination level of the lubricant which is the monitoring target based on a positional relationship on the chromaticity coordinate between the data regarding the chromaticity of the lubricant and the data of the deterioration curve, and a positional relationship on the chromaticity coordinate between the data of the contamination level threshold curve and the data of the deterioration curve. According to still another preferred aspect of the present invention, there is provided a method for diagnosing a lubricant, which is executed by an information processing apparatus including an input device, a processing device, a storage device, and an output device. In the diagnosing method, data of a deterioration curve, which indicates a transition in a chromaticity of the lubricant on a chromaticity coordinate as the lubricant deteriorates, is prepared, and data of a contamination level threshold curve, which indicates a threshold value for a contamination level of the lubricant on the chromaticity coordinate by the chromaticity of the lubricant, is prepared. Then, chromaticity information of the lubricant which is a diagnosis target is obtained to specify a position on the chromaticity coordinate, the chromaticity information being optically measured, and a relative contamination level of the lubricant is derived from a positional relationship between the position of the chromaticity information of the lubricant which is the diagnosis target on the chromaticity coordinate, the deterioration curve, and the contamination level threshold curve. According to the present invention, it is possible to quantitatively diagnose the contamination and the deterioration of the additive of the lubricant. Tasks, configurations, and effects other than those described above will become apparent from the following description of embodiments.

BRIEF DESCRIPTION OF THE DRAWINGS

FIG. 4B is a graph showing a method for obtaining a relative contamination amount in the present invention;

DETAILED DESCRIPTION OF THE PREFERRED EMBODIMENTS

In these examples, the contamination and the deterioration of a lubricant are quantitatively diagnosed using chromaticity data obtained based on measurement data of an optical sensor, a result is notified, and a necessary maintenance is performed. Firstly, the circumstances leading to the present invention will be described before describing embodiments of the present invention in detail. In recent years, as a technique of evaluating the residual life of a component makes progress, the preventive preservation and the scheduled maintenance of a machine including rotary components (hereinafter, referred to as a rotary machine) becomes widely used. Since a decrease in lubrication function caused by oxidation deterioration of the lubricant or contamination particles such as wear powder and dust in the lubricant induces wear damage to the rotary components such as bearings and gears, which leads to a failure of the rotary machine, a lubricant monitoring technique is particularly important. Incidentally, in the following specification, a decay in the lubricant or an additive of the lubricant, for example, a change in the concentration of the additive is referred to as "deterioration (deterioration level)", and the mixing of wear powder, dust, water, or the like into the lubricant is referred to as "contamination (contamination level)".

<1. Example of Wind Power Generator to which Lubricant Monitoring Technique is Applied>

In a wind power generator which is one example of an apparatus to which the present invention is applied, a lubricant or the like is used to reduce a mechanical frictional coefficient between components. Hereinafter, a lubricant monitoring technique will be described using the lubricant of the wind power generator as an example.

Figure 1:
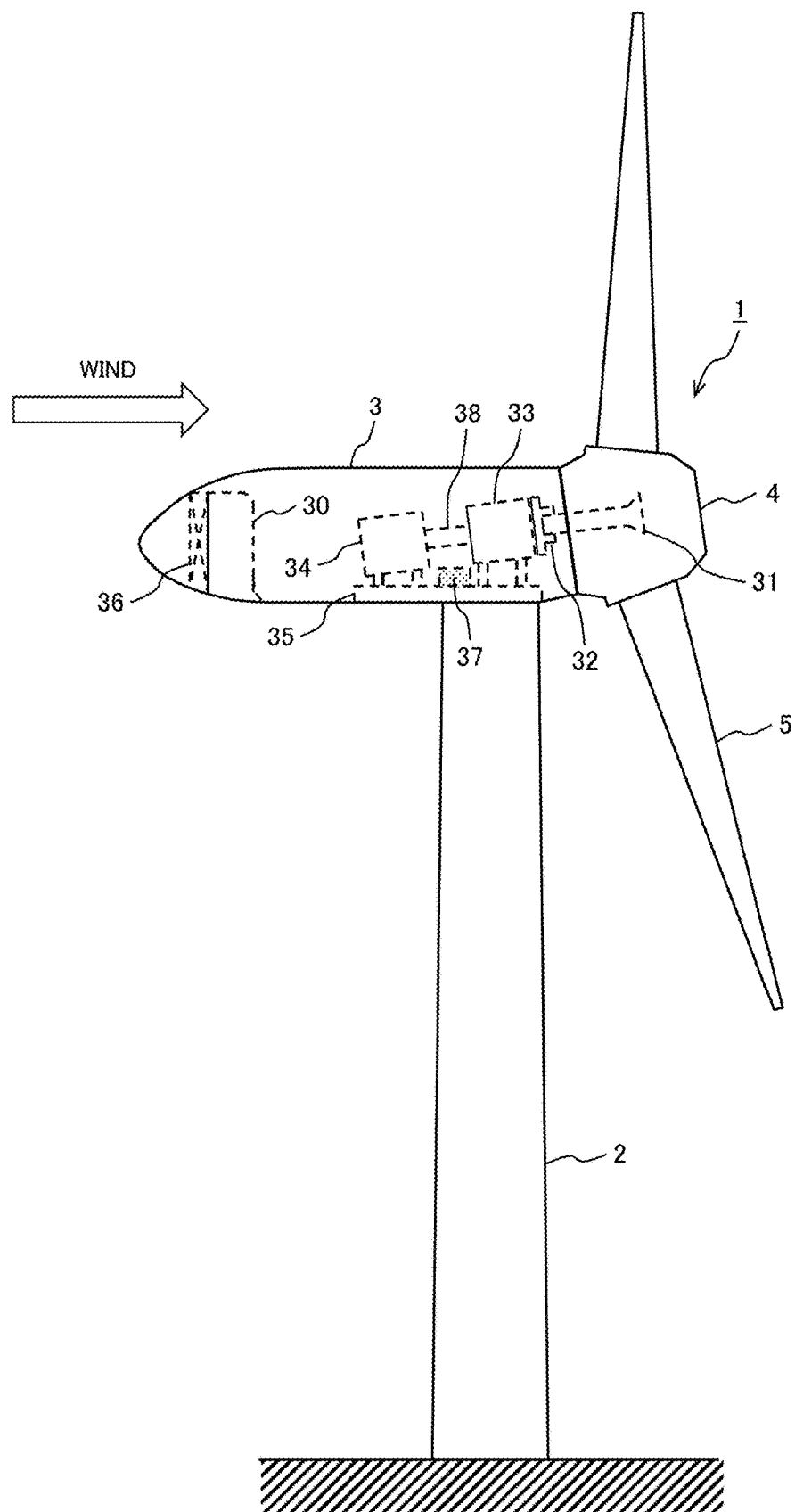
FIG. 1 is a schematic configuration diagram of the entirety of a wind power generator that is one example of an apparatus to which the present invention is applied.

FIG. 1 is a schematic configuration diagram of the entirety of a downwind wind power generator. In FIG. 1, each device disposed inside a nacelle 3 is indicated by the dotted line. As illustrated in FIG. 1, a wind power generator 1 includes a blade 5 that receives wind to rotate, a hub 4 that supports the blade 5, the nacelle 3, and a tower 2 which supports the nacelle 3 such that the nacelle 3 is rotatable in a horizontal plane.

The wind power generator 1 includes the following components inside the nacelle 3: a main shaft 31 that is connected to the hub 4 and rotates together with the hub 4, a shrink disk 32 coupled to the main shaft 31, a gearbox 33 that is connected to the main shaft 31 via the shrink disk 32 and increases a rotation speed, and a generator 34 that rotates a rotor via a coupling 38 at the rotation speed increased by the gearbox 33, to generate electricity.

A portion which transmits the rotation energy of the blade to the generator 34 is referred to as a power transmission portion, and in this example, the power transmission portion includes the main shaft 31, the shrink disk 32, the gearbox 33, and the coupling 38. Then, the gearbox 33 and the generator 34 are held on a main frame 35. In addition, one or a plurality of oil tanks 37 which stores a lubricant for the lubrication of the power transmission portion are installed on the main frame 35.

In addition, a radiator 36 is disposed closer to a windward side than a nacelle partition wall 30 inside the nacelle 3. Cooling water which is cooled using outside air by the radiator 36 circulates through the generator 34 or the gearbox 33 to cool the generator 34 or the gearbox 33.

The lubricant is used in a large number of rotary components in the wind power generator. For example, the lubricant is supplied to the main shaft 31, the gearbox 33, and the generator 34 in FIG. 1 and bearings such as a yaw bearing and a pitch bearing (not illustrated). The controlling of an output by changing the pitch angle of the blade according to the wind speed is blade pitch control, and nacelle orientation control is yaw control.

It is necessary to supply the lubricant to such movable parts. The lubricant reduces the friction of the rotary parts to prevent wear or damage of the components or an energy loss. However, when a decrease in lubrication performance caused by the deterioration of the lubricant over time, or contamination by the mixing of wear particles, dust, or the like into the lubricant occurs, the frictional coefficient increases, and a risk of failure of the wind power generator increases.

When the wind power generator fails, since there occurs a significant cost loss such as the cost of replacing a failed component or a reduction in power generation income during power outage, it is desirable to prepare countermeasures such as early component procurement and a reduction in power outage period by a residual life prediction and a predictive detection. Particularly, when the performance of the lubricant decreases, since a risk of failure of the gearbox which is an important component increases, a technique for detecting the deterioration or contamination of the lubricant to estimate the residual life or the replacement timing of the lubricant as early as possible is important.

<2. Method for Evaluating Properties of Lubricant and Various Additives>

As the parameters of monitoring targets for evaluating the properties of the lubricant, various parameters such as viscosity, total acid number measurement, and component element analysis can be considered.

However, for example, when the lubricant of the wind power generator is assumed as a monitoring target, since a synthetic oil which is chemically very stable is used as the lubricant of the gearbox of the wind turbine generator and the viscosity of the synthetic oil hardly changes in the evaluation of the properties by the viscosity, only the viscosity is not suitable as an index for the estimation of the residual life. In addition, since a synthetic oil which is very stable against oxidation is used as the lubricant of the gearbox of the wind turbine generator and the total acid number of the synthetic oil hardly changes in the measurement of the total acid number indicating a oxidation deterioration, only the total acid number is not suitable as an index for the estimation of the residual life.

In addition, a method for measuring fine particle powder or moisture contained in the lubricant can be also considered; however, since wear or leak may have already occurred at the time these contents are detected in the lubricant, it is desirable to perform an earlier predictive detection. In addition, since the lubricant of the gearbox of the wind turbine generator has a high viscosity, and circulates in a state where a large number of bubbles are mixed into the lubricant, it is difficult to distinguish the bubbles from particles by a particle measurement method where a particle counter or an iron powder concentration meter is installed to perform the measurement of particles. In addition, it is in principle impossible to measure the consumption of the additives of the lubricant which will be described later by the particle counter or the iron powder concentration meter.

Due to the foregoing reasons, in order to early estimate the residual life of the lubricant of the wind power generator, a new performance evaluation method for the lubricant of the wind power generator is required.

By the way, as described above, the lubricant contains various additives so as to maintain the lubrication performance. Examples of the additives include a load-bearing additive such as an oiliness agent, an anti-wear agent, or an extreme-pressure additive (extreme-pressure agent), an antioxidant, and a defoamer. The lubricant of the gearbox of the wind power generator contains a single or a plurality of the additives.

The oiliness agent is adsorbed to a metal surface to form an adsorption film, and the adsorption film serves to prevent direct contact between metals which are in a boundary lubrication state, and reduce the friction and wear of the metals. A higher fatty acid, a higher alcohol, an amine, an ester, a metal soap, or the like having high adsorption to a metal surface is used as the oiliness agent.

The anti-wear agent is more effective in preventing wear under severe load conditions than the oiliness agent, and generally, a phosphate, a phosphite, or a thiophosphate is often used as the anti-wear agent. The anti-wear agent is used in a turbine oil, an anti-wear hydraulic oil, and the like, and particularly, a zinc dialkyldithiophosphate (ZnDTP: also referred to as ZDDP) has also antioxidant performance.

On a contact surface in a high load state under the most severe conditions of a boundary lubrication state, the temperature of the friction surface is very high and the adsorption film formed by the oiliness agent is desorbed to lose the effect; however, since the extreme-pressure additive is a chemically active substance containing sulfur, chlorine, phosphorus, or the like, the extreme-pressure additive reacts with the metal surface to form a compound containing sulfur, chlorine, phosphorus, or the like, and a coating having a small shearing force is formed to prevent wear, seizure, and fusion.

Generally, the extreme-pressure additive is a substance containing sulfur, chlorine, phosphorus, or the like, and in addition to a sulfurized grease, a sulfurized ester, a sulfide, a chlorinated hydrocarbon, or the like, a lead naphthenate or a compound containing two or more elements of sulfur, phosphorus, and chlorine in the same molecule is also used as the extreme-pressure additive. Specific examples of the extreme-pressure additive include a sulfurized palm oil, a sulfurized fatty ester, a dibenzyl disulfide, an alkyl polysulfide, an olefin polysulfide, a zantic sulfide, a chlorinated paraffin, a methyl trichlorostearate, a lead naphthenate, an alkylthiophosphate amine, a chloroalkyl xanthate, a phenol thiocarbamate, a triphenyl phosphorothionate (TPPT), and a 4,4'-methylenebis(dithiocarbamate).

The antioxidant is used to prevent a deterioration caused by the oxidation of a base oil. There are three types of the antioxidants. The three types of antioxidants are a free radical inhibitor that inhibits the generation of free radicals in the early stage of oxidation and stops a chain of oxidation reaction of hydrocarbons, a peroxide decomposer that plays a role in decomposing the generated peroxide and converting the generated peroxide into a stable non-free radical compound, and a metal deactivator that forms a strong adsorption film (inert anti-corrosion film). The role of the metal deactivator is to prevent iron or copper from being dissolved due to the metal corrosiveness of the peroxide generated by the oxidation of the lubricant.

Specific examples of the antioxidant include phenol derivatives (2,6-di-tert-butyl-p-cresol (BHT), 2,6-di-tert-butyl-p-phenol (DBP), 4,4'-methylenebis(2,6-dialkylphenol), and the like), amine derivatives(2,6-dialkyl-α-dimethylaminoparacresol, 4,4'-tetramethyldiaminodiphenylmethane, octylated phenylnaphthylamine, di-octyl-diphenylamine, dinonyl-diphenylamine, phenothiazine, 2,2,4-trimethyldihydroxyquiniline, and the like), a metal dithiophosphate, an alkyl sulfide, 1,4-dioxydianthraquinone (alias: quinizarin), 1,2-dioxydianthraquinone (alias: alizarin), benzotriazole, and alkylbenzotriazole.

A silicone-based defoamer, a surfactant, a polyether, and a higher alcohol are known as examples of the defoamer. When bubbles occur in a high-viscosity lubricant such as a gear oil, the bubbles are unlikely to disappear and cause adverse effects such as the occurrence of damage to components due to a decrease in lubrication performance, the occurrence of cavitation, a decrease in hydraulic efficiency, and a decrease in cooling capacity.

These additives are required to be contained in the lubricant at a predetermined ratio (concentration) so as to maintain the desired lubrication performance. For example, when the concentrations of the extreme-pressure agent and the anti-wear agent are reduced, the wear of a machine using the lubricant is promoted.

<3. Evaluation of Properties of Lubricant by Optical Sensor>

The concentration of the additive of the lubricant can be measured using chromaticity data obtained based on measurement data of an optical sensor. The optical sensor described in JP 2012-117951 A and the like can be used as a sensor that monitors the deterioration of the lubricant. The optical sensor includes a light source such as a white LED that emits visible light, and a visible light photodetector (RGB color sensor), and measures the chromaticity of the lubricant by measuring the transmittance of the visible light that is transmitted through the lubricant.

There is a positive correlation between the concentration of the additive in the lubricant and the degree of coloring (chromaticity) of the lubricant. The chromaticity is displayed by a color difference (ΔE) that is calculated in a color space formed of a combination of RGB. According to the definition of ΔE, $\Delta E = (R^2 + G^2 + B^2)^{1/2}$.

R, G, and B imply three primary colors (red, green, and blue) of light in additive mixing, and are expressed as (R, G, B) in the numerical display of the color coordinate. Incidentally, the RGB chromaticity encoded at 24 bits per pixel (24 bpp) is represented by three 8-bit unsigned integers (from 0 to 255) indicating the luminances of red, green, and blue. For example, (0, 0, 0) indicates black, (255, 255, 255) indicates white, (255, 0, 0) indicates red, (0, 255, 0) indicates green, and (0, 0, 255) indicates blue. Incidentally, as the display of the chromaticity, in addition to an RGB color system, there are many types of color systems such as an XYZ color system, an L*a*b* color system, and an L*u*v* color system, and since the chromaticity can be mathematically converted and deployed in various color systems, the chromaticity may be displayed in another color system.

The reason that the consumption level of the additive which is an index for the deterioration of the lubricant has a correlation with the chromaticity is described as follows. When the additive is applied to a sliding surface of the gear or the bearing, the additive is decomposed, and the decomposition products of the additive are oxidation products such as a phenolic oxide and a quinone and are colored in yellow to reddish brown. For example, when the BHT which is an antioxidant or the TPPT which is an extreme-pressure agent is decomposed, a colored compound is formed. The BHT and the TPPT are almost colorless. Due to the foregoing reasons, the deterioration of the lubricant has a positive correlation with an increase in the colored compound which is the decomposition product. Therefore, the deterioration level of the lubricant is obtained by measuring the chromaticity.

There is a case where the lubricant contains a plurality of the additives. Also in this case, when a relationship between the concentration of each of the additives in the lubricant which is obtained by high-speed liquid chromatography or the like and the chromaticity of the lubricant which is obtained based on measurement data of the optical sensor is obtained in advance, during the monitoring of the lubricant, the concentration of each of the additives in the lubricant can be measured based on the chromaticity of the lubricant which is obtained based on the measurement data of the optical sensor.

<4. Method for Evaluating Relative Contamination Level Using Deterioration Curve>

The consumption (deterioration) of the additive of the lubricant and the contamination of the lubricant can be distinguished from each other based on the measurement data of the optical sensor. The description will be given below.

Regarding the "deterioration" of the lubricant which has to be monitored by the optical sensor, an oxidation stability test, which is a test that forcibly deteriorates the lubricant within a short time at a high temperature under the blowing or pressurizing of oxygen or air and in the presence of a catalyst, is known as an accelerated deterioration test.

Major examples of the oxidation stability test include a turbine oil oxidation stability test (TOST), a rotating bomb oxidation test (RBOT), and an internal combustion engine lubrication oxidation stability test (ISOT). A deteriorated oil which is obtained by causing an oil to be subjected to a test where only the reaction time is changed and the reaction conditions are the same as those of the lubricant has the same deterioration behaviors as those of the lubricant used in the wind turbine or the like.

Figure 2:
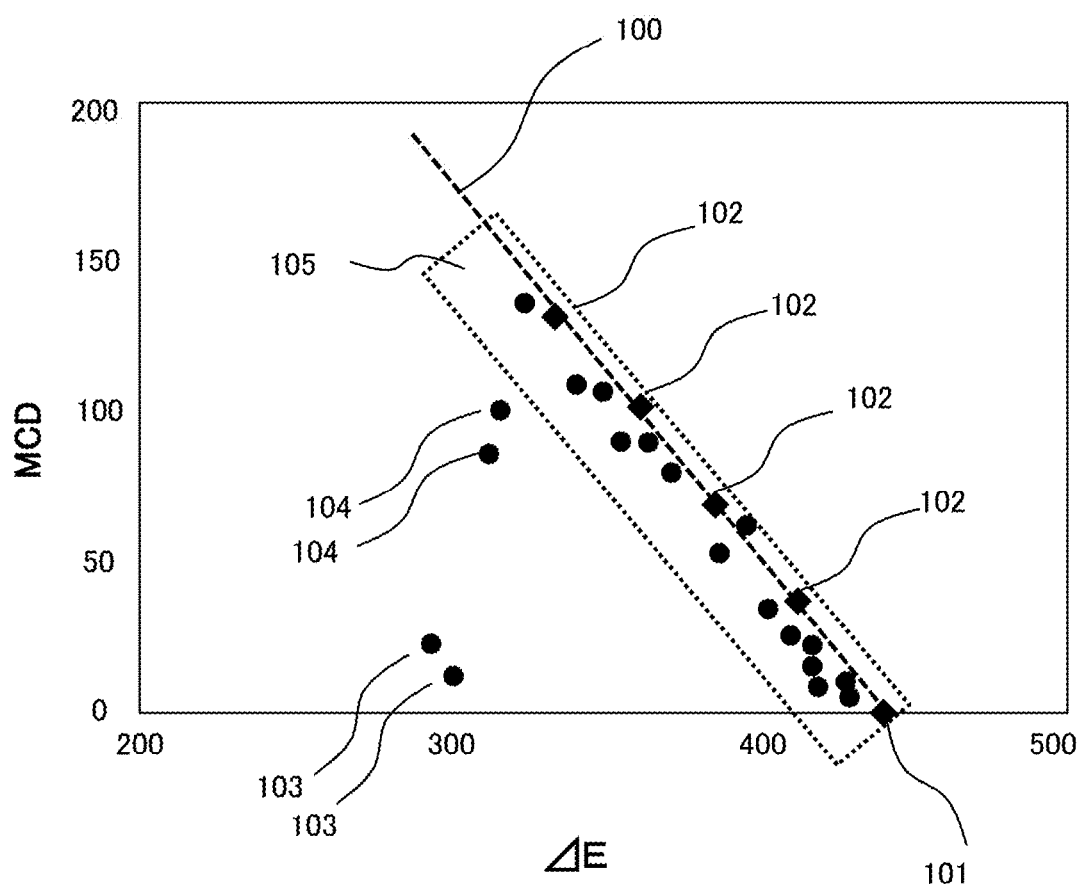
FIG. 2 is a graph showing a deterioration curve and a distribution of normal and abnormal samples.

FIG. 2 is a graph showing chromaticity sensor data ΔE and MCD of a deteriorated oil of the lubricant of the gearbox of the wind turbine, which is subjected to the ISOT tests that are performed while changing the reaction time to four values. The definition of the MCD is a difference between a maximum value and a minimum value among R, G, and B color coordinates. Intuitively, the larger the MCD is, the brighter the color is, and the smaller the MCD is, the less the color is. In addition, the larger the ΔE is, the closer to white the color is, and the smaller the ΔE is, the closer to black the color is.

Square marks in FIG. 2 indicate oxidation test samples 102 in the ISOT test and a new oil 101. The new oil 101 which is assumed to have no deterioration is plotted at the lower right. In addition, four types of the oxidation test samples which are obtained by changing the reaction time of the ISOT (namely, changing the progress of the deterioration level) are plotted. The plots of the oxidation test samples 102 and the new oil 101 express the progress of deterioration of the lubricant, and are referred to as a deterioration curve 100. Here, the deterioration curve 100 can be linearly approximated and is shown by the straight line in FIG. 2. The plot is shifted to the upper left from a state of the new oil 101 on the deterioration curve 100 as the deterioration of the lubricant makes progress. Namely, as the deterioration makes progress, the MCD increases, and the ΔE decreases.

Round marks in FIG. 2 are plots of chromaticity sensor data of various samples that are sampled from the gearbox of the wind turbine and have different deterioration levels or different contamination levels. Normal samples having contamination levels within a normal range 105 with respect to a specified value are plotted in the vicinity of the deterioration curve 100. Samples 103 contaminated by water and samples 104 contaminated by wear powder are plotted on a left side (side where the ΔE is small) of the normal range 105.

Figure 3:
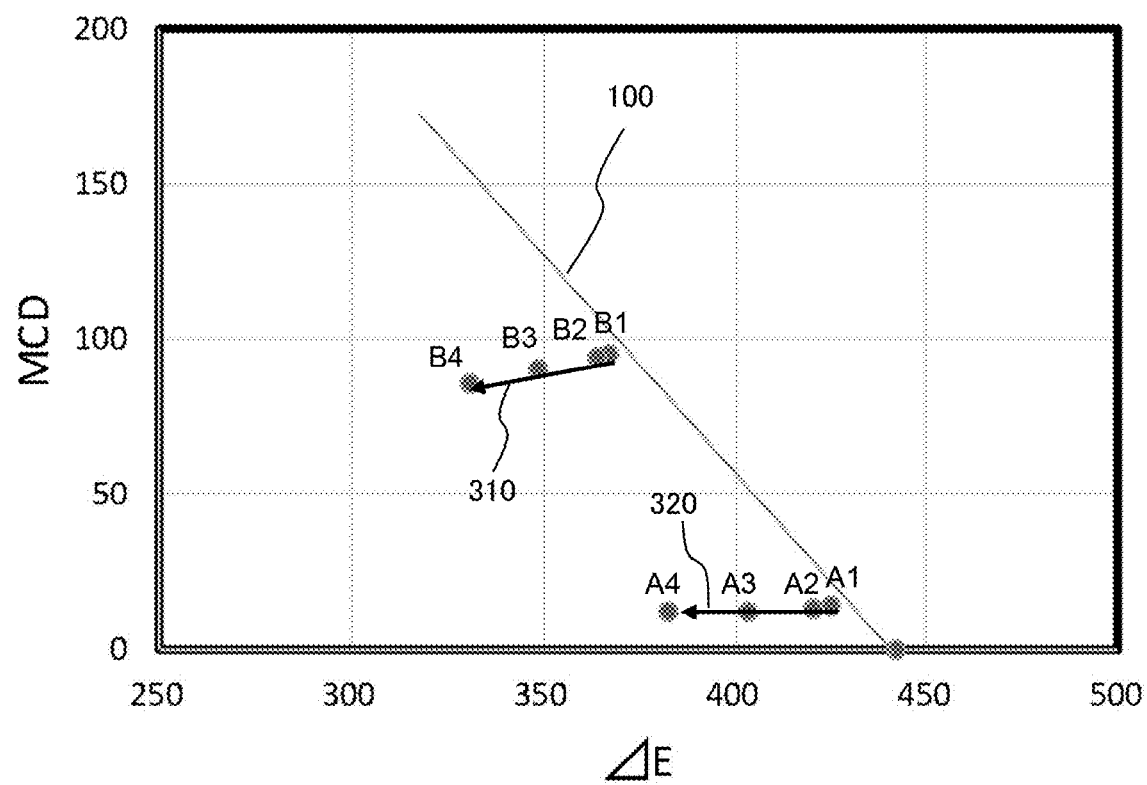
FIG. 3 is a graph showing a result of calculation of a shift of plots caused by the contamination of a lubricant.

FIG. 3 shows a result of performing a simulation as to how the chromaticity sensor data changes when the contamination of the lubricant occurs due to water or solid particles. The axes of the graph are the same as those in FIG. 2.

In the contamination by water or solid particles, there is no dependence on wavelength, and the transmittance of visible light decreases. It is apparent that when there occurs a decrease of 1%, 5%, and 10% in the transmittance of each of two types of samples A1 and B1 having different deterioration levels, as with A2 to A4 and B2 to B4, the color coordinate changes and approximately, the MCD value hardly changes, whereas the ΔE value significantly decreases.

When foreign matter is mixed into the lubricant, the color coordinate is considered to change as indicated by arrows 310 and 320 (expediently, referred to as "contamination curves") due to the absorption of light by the foreign matter. A plurality of the contamination curves can be set depending on the deterioration level of the lubricant before contamination. On each of the contamination curves, a value where the contamination makes progress to a level which is not suitable for use can be defined as a contamination limit, and a line connecting the contamination limits of the contamination curves can be defined as a contamination level threshold curve. For example, when A4 and B4 are the contamination limits in FIG. 3, the contamination level threshold curve can be defined by a line connecting A4 and B4.

Figure 4A:
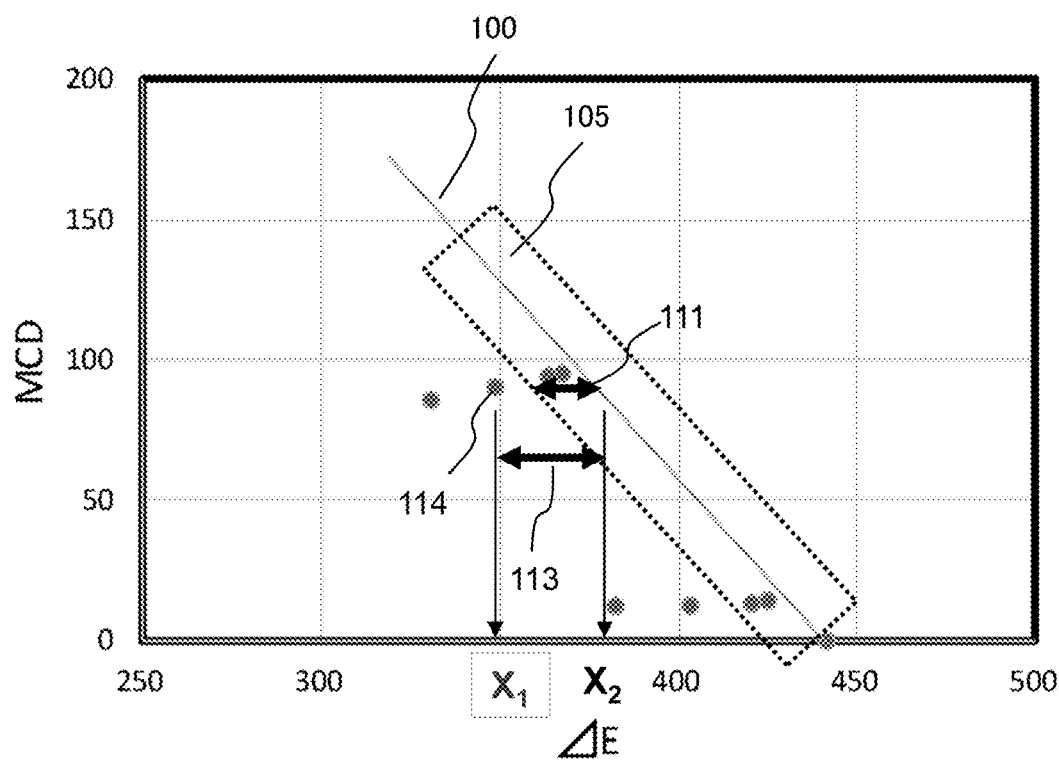
FIG. 4A is a graph showing a method for obtaining a relative contamination amount in the present invention.

FIGS. 4A and 4B show a principle of evaluating the contamination level of a lubricant sample based on the deterioration curve 100. In this example, the deterioration curve 100 is linearly approximated. In determining the subsequent response, it is preferable to display the contamination level in an easy-to-understand manner rather than displaying the contamination level of the lubricant sample by the color coordinate or chromaticity.

As shown in FIG. 4A, regarding the contamination level, the value of a contamination limit (Z) 111 is determined in advance from the degree of deviation from the deterioration curve 100. In this example, the degree of deviation is a distance in a ΔE direction. The contamination limit can be determined as a threshold value that determines whether or not the contaminated lubricant can withstand use based on experiments and experiences. A threshold curve which defines the contamination limit on the chromaticity coordinate is a contamination level threshold curve 401 shown in FIG. 4B. In this example, for easy understanding, the contamination level threshold curve 401 is approximated to a straight line parallel to the deterioration curve 100. Therefore, the value of the contamination limit (Z) 111 is the same for lubricants having any deterioration levels. Naturally, the contamination level threshold curve 401 may be a straight line having a different slope from that of the deterioration curve 100, and in that case, the value of the limit contamination amount (Z) 111 differs depending on the deterioration level of the lubricant. According to the study by the inventors, it is possible to linearly approximate the contamination level threshold curve 401 and the deterioration curve 100 in the diagnosis of the lubricant of the wind turbine which is a target. A more generalized description will be given later in a third example.

Then, when a relative value between a contamination amount 113 equivalent to a distance from the deterioration curve 100 in sensor data of a lubricant sample 114 and the contamination limit is displayed as a relative contamination level, it is easy to understand the degree of abnormality. Incidentally, in this example, the contamination limit (Z) and the contamination amount are defined as distances from the deterioration curve 100 in an x-axis direction (distances of the ΔE); however, the contamination limit (Z) and the contamination amount may be defined in another way.

Here, the definition of and a method for obtaining the relative contamination level will be described. When the coordinate (ΔE, MCD) of the lubricant sample 114 which is contaminated and shown by plots in the drawing is $(X_1, Y_1)$, the contamination amount of the lubricant sample 114 is expressed by $X_2-X_1$.

As schematically shown in FIG. 4A, the periphery of the deterioration curve 100 is the normal range 105, and at least a part of the boundary of the normal range 105 is the contamination level threshold curve. A region outside the normal range 105 is an abnormal region. In a typical example, a lubricant contaminated by water or particles is shifted to an abnormal region on a left side of the deterioration curve 100.

The description will be given again with reference to FIG. 4B. The coordinate of a contaminated sample is indicated by $(X_1, Y_1)$. When the contamination limit 111 which is a contamination amount from the deterioration curve 100 to the contamination level threshold curve 401 (here, linearly approximated) is 100%, a relative contamination level $Z_1$ (%) of the lubricant sample 114 is obtained by $Z_1=((X_2-X_1)/Z)*100$. When the deterioration curve 100 is expressed by the following equation $y=-Ax+B$, $X_2$ can be obtained as follows.

$$X_2=(B-Y_1)/X$$

Regarding the deterioration of the lubricant, a deterioration threshold value 402 is provided on the deterioration curve 100, the deterioration level of the new oil 101 is set to 0%, a distance 403 from the deterioration threshold value 402 to the new oil is set to a deterioration level of 100%, a distance 404 from the coordinate of a sample to the new oil is relatively displayed (%); and thereby, the deterioration level can be displayed as a relative value to be easily understood. The deterioration threshold value 402 which is a deterioration level of 100% can be set to the limit life (for example, a life determined by an oil maker or determined based on experiments and experiences) of the lubricant which is determined in advance.

<5. Method for Detecting Abnormality by Transition in Contamination Over Ttime>

The deterioration of the lubricant makes a transition on the deterioration curve almost without increase or decrease with use; however, regarding the contamination of the lubricant, since an oil filter which traps contamination particles is installed in the rotary machine, the contamination particles may be reduced. In addition, it is known that the concentration of contamination particles in the lubricant is reduced since the contamination particles subside when the operation of the rotary machine slows down or stops, or while the rotary machine is in use, the contamination particles increase with a change in load amount or rotation speed, and it is possible to perform a diagnosis with higher accuracy when performing the diagnosis using a correlation between the relative contamination level and contamination level variation factors thereof.

Figure 5A:
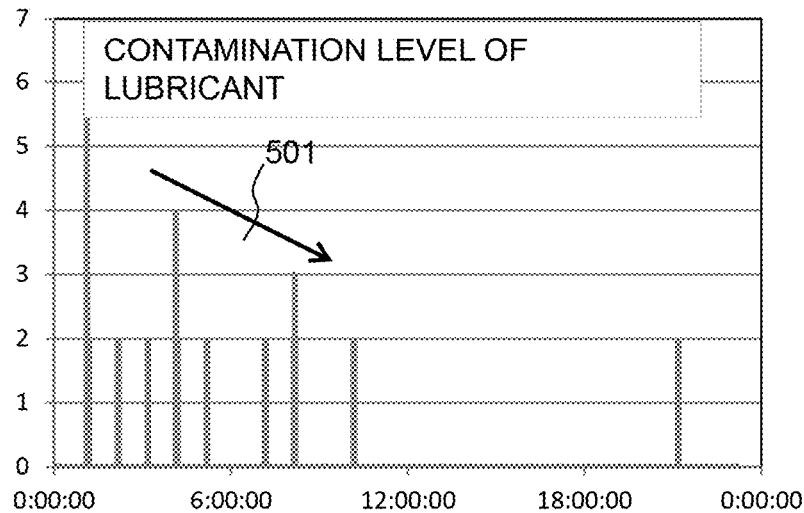
FIGS. 5A and 5B is a graph showing a correlation between a contamination level of the lubricant and an output of a wind turbine.
Figure 5B:
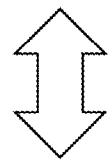
Figure 5B:
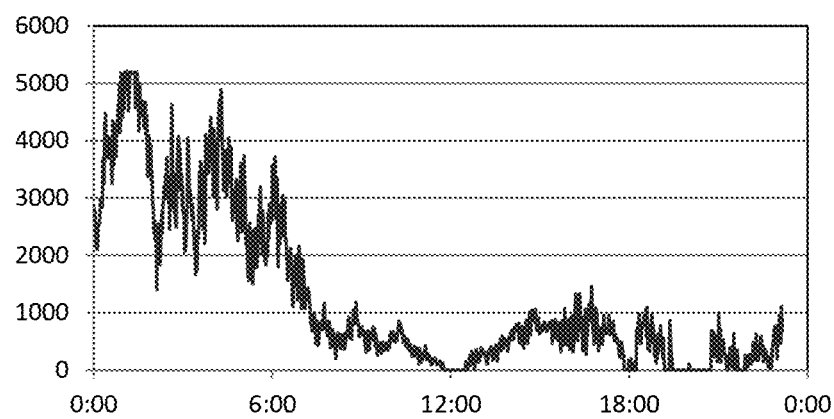
Figure 6A:
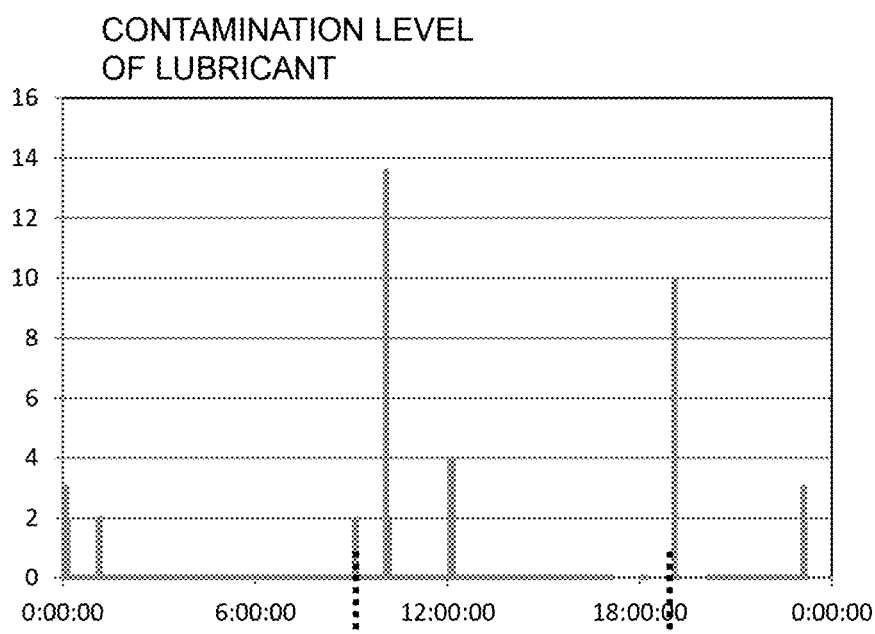
FIGS. 6A and 6B is a graph showing a correlation between the contamination level of the lubricant and the output of the wind turbine.
Figure 6B:
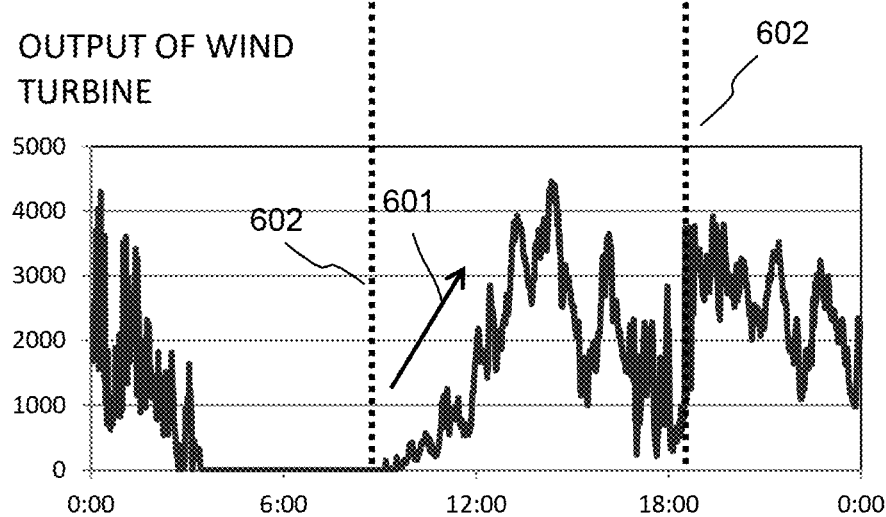

FIGS. 5 and 6 are graphs describing a correlation between the contamination level of the lubricant and the output of the wind turbine. In FIG. 5A and FIG. 6A, the horizontal axis indicates time and the vertical axis indicates the contamination level of the lubricant (arbitrary unit), and in FIG. 5B and FIG. 6B, the horizontal axis indicates the same time zone as in FIG. 5A and FIG. 6A, and the vertical axis indicates the output of the wind turbine.

As shown in FIG. 5, when the output of the wind turbine is on a decreasing tendency, also the contamination level is on a reduction tendency 501. The reason is considered to be due to the particles being trapped by the oil filter or subsiding as described, and can be determined to be normal. In addition, as shown in FIG. 6, when the output of the wind turbine is on an increasing tendency 601 or a timing is at an increasing timing 602, the contamination level is on a rising tendency. The reason is considered to be due to the particles being increased by the acceleration of a rotary shaft or the like, and can be determined to be normal.

Therefore, it is considered that the phenomenon of an increase in the contamination level having the correlation with the output of the wind turbine as shown in FIGS. 5 and 6 is in a normal category. However, it is apparent that when the contamination level is not in synchronization with the output of the wind turbine and not in synchronization with a transition in the output of the wind turbine, for example, when the contamination level continuously rises, there is a high possibility of an abnormality occurring.

Figure 7:
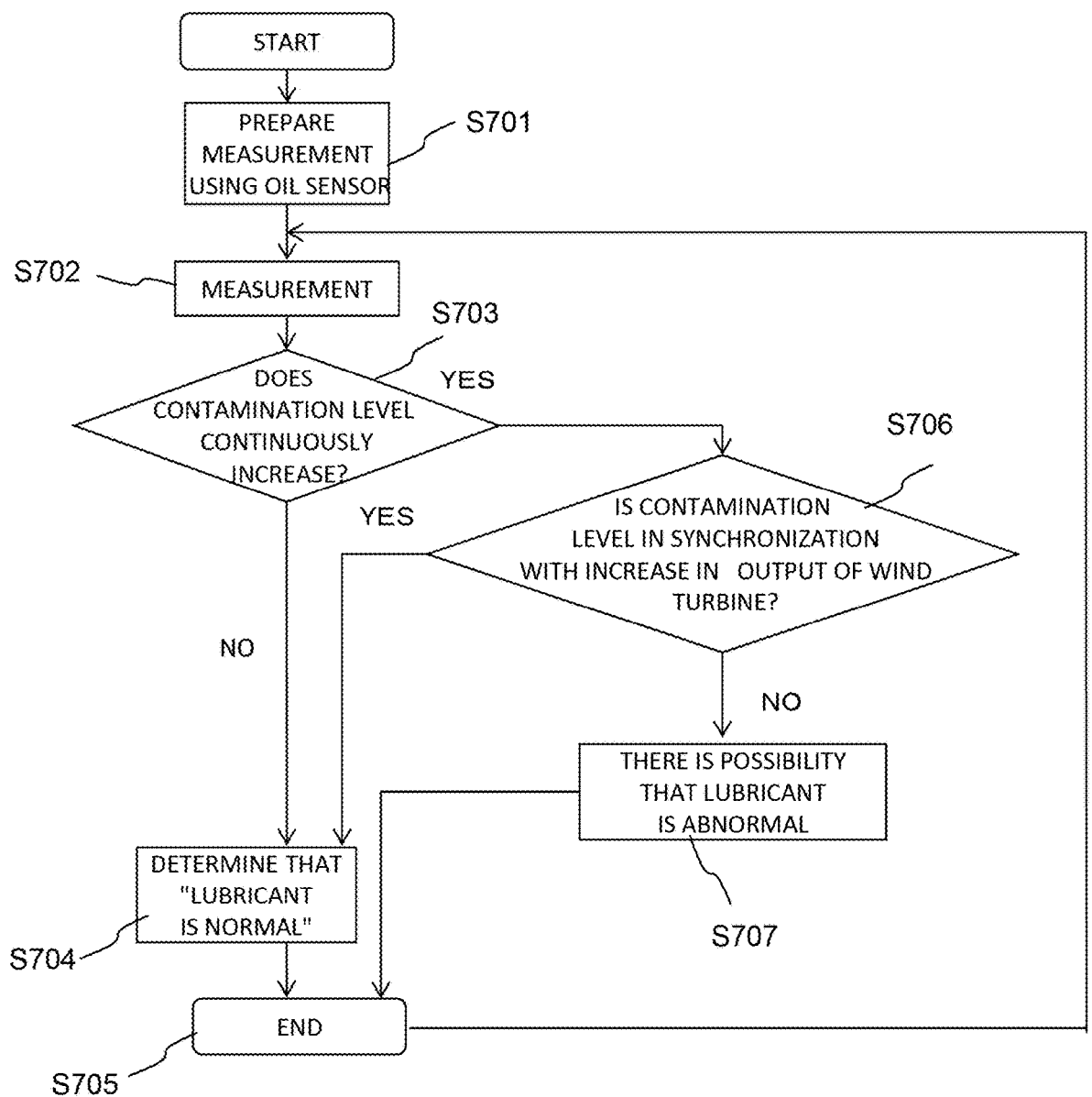
FIG. 7 is a flowchart to which a diagnosis is performed based on the correlation between the contamination level of the lubricant and the output of the wind turbine.

FIG. 7 is an example of a flow of the diagnosis of the contamination level based on the foregoing study. In a step S701, for example, a measurement using an optical oil sensor by the method described in JP 2012-117951 A is prepared. In a step S702, the color of the lubricant is measured, and the ΔE and the MCD are calculated. The measurement is periodically performed, and a transition in the contamination level over time is monitored. In a step S703, it is determined whether or not the contamination level continuously increases (monotonically increases). When the contamination level does not continuously increase, in a step S704, it is determined that the treated lubricant is normal, and the next measurement is waited in a step S705.

When in the step S703, the contamination level continuously is determined to increase, in a step S706, it is determined whether or not the transition in the contamination level is in synchronization with the output of the wind turbine. When the transition in the contamination level is in synchronization with the output of the wind turbine, in the step S704, it is determined that the treated lubricant is normal, and the next measurement is waited in the step S705. When the transition in the contamination level is not in synchronization with the output of the wind turbine, in a step S707, it is determined that the treated lubricant has the possibility of being abnormal, and in the step S705, a warning display or the like is performed for an administrator or operator.

In the determination of a correlation between the contamination level of the lubricant and an operation parameter such as the output of the wind turbine in the step S706, for example, there is a method for determining that "there is a correlation" when a correlation factor of average values of data per minute is 0.5 or greater, and determining that "there is no correlation" when the correlation factor is less than 0.5. In this case, a correlation between the values of the contamination level and the operation parameter per one second or ten seconds may be evaluated. A correlation factor of 0.4, 0.6, or the like may be set as a boundary depending on the type or state of the machine.

In a summary of the diagnosis of contamination of the lubricant, when the relative contamination level exceeds 100% and the correlation factor between the contamination level and the critical machine operation parameter such as an output is less than a boundary value, it is determined that "the contamination level is abnormal". The time range where the correlation factor is obtained can be determined by the frequency of a change in the operation parameter, and a determination is performed with a time resolution of, for example, the latest one hour or the latest twelve hours.

In the above description, the output of the wind turbine is provided as an example of the operation parameter, and it is possible to use a parameter such as the number of revolutions of the shaft or the wind speed of which the relationship with the contamination level of the lubricant can be confirmed.

In the diagnosis of the contamination and the deterioration of the lubricant, it is necessary to obtain the correlation between the operation parameter of the machine and the contamination and the deterioration of the lubricant. The "contamination" may be firstly determined, and when the contamination is determined to be normal, the "deterioration" may be determined and the residual life of the lubricant may be calculated. The reason is that in many cases, the "contamination" of the lubricant has a higher risk of failure of the machine and it is necessary to early make a notification to the owner of the machine or a business owner. When the contamination level of the lubricant is within the normal range, it is preferable to perform the diagnosis of the residual life such as "how many years can the lubricant be used?" and make a notification.

Hereinafter, embodiments of the present invention will be described in detail with reference to the drawings. However, the present invention is not interpreted as being limited to the description of the embodiments below. Those skilled in the art easily understand that changes can be made to a specific configuration of the present invention without departing from the concept or intent of the present invention.

In the configuration of the invention described below, the same reference signs are used in common for the same parts or parts having the similar functions between different drawings, and repeated descriptions will be omitted.

When there are a plurality of the same elements or elements having the similar functions, the description may be given with different subscripts attached to the same reference signs. However, when it is not necessary to distinguish the plurality of elements from each other, the description may be given with the subscripts omitted.

Notations such as "first", "second", and "third" in this specification and the like are attached to identify components, and do not necessarily limit the number, order, or contents thereof. In addition, a number for identifying a component is used in each context, and a number used in one context is not limited to necessarily indicating the same configuration in another context. In addition, a component identified by a number is not prevented from having the function of a component identified by another number.

In order to facilitate the understanding of the invention, the position, size, shape, range, and the like of each component illustrated in the drawings and the like may not represent the actual position, size, shape, range, and the like. For this reason, the present invention is not necessarily limited to the positions, sizes, shapes, ranges, and the like disclosed in the drawings and the like.

FIRST EXAMPLE

In the present example, a system of monitoring a lubricant supplied to mechanical drive units of the wind power generator will be described. This system includes an input device, a processing device, a storage device, and an output device. The storage device stores data of a deterioration curve, data of a deterioration threshold value, and data of a contamination level threshold curve of the lubricant, and the relative contamination level and the relative deterioration level of the lubricant can be measured based on data of an optical sensor that measures the chromaticity of the lubricant.

In addition, in this example, a method for monitoring the lubricant of the wind power generator using a server including the processing device, the storage device, the input device, and the output device and using an optical lubricant sensor will be described. This method executes a first step of acquiring chromaticity data of the lubricant of the wind power generator, a second step of measuring the concentration of an additive contained in a sample, a third step of chronologically storing the measured concentration of the additive as additive concentration data in the storage device, and a fourth step of causing the processing device to process the additive concentration data to estimate the time taken for the concentration of the additive to reach a predetermined threshold value.

(1. Entire Configuration of System)

Figure 8:
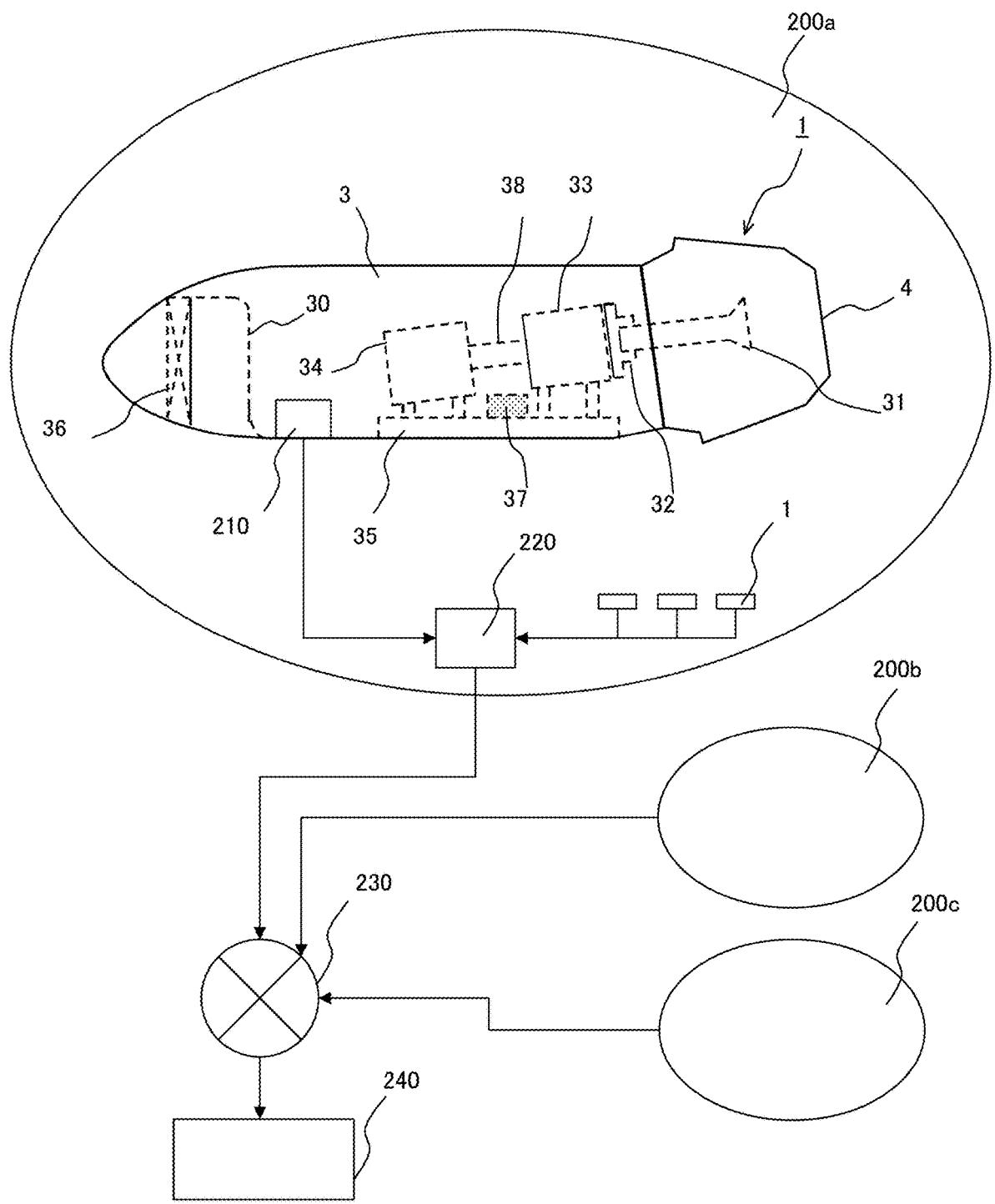
FIG. 8 is a schematic diagram of a system of monitoring a lubricant of a wind power generator including a lubricant supply system.

FIG. 8 illustrates a schematic diagram of the system of monitoring the lubricant of the wind power generator including a lubricant supply system. The main shaft 31, the gearbox 33, the generator 34, and bearings such as a yaw bearing and a pitch bearing (not illustrated) are provided inside the nacelle 3, and the lubricant is supplied from the oil tank 37 to these components.

As illustrated in FIG. 8, usually, a plurality of the wind power generators 1 are installed at the same site, and are collectively referred to as a farm 200a or the like. Various sensors (not illustrated) are installed in the lubricant supply system of each of the wind power generators 1, and sensor signals which reflect the state of the lubricant are aggregated in a server 210 inside the nacelle 3. In addition, the sensor signals which are obtained from the server 210 of each of the wind power generators 1 are transmitted to an aggregation server 220 disposed in each farm. Data from the aggregation server 220 is transmitted to a central server 240 via a network 230. Data from other farms 200b and 200c is also transmitted to the central server 240. In addition, the central server 240 can transmit an instruction to each of the wind power generators 1 via the aggregation server 220 and the server 210.

(2. Disposition of Sensors)

Figure 9:
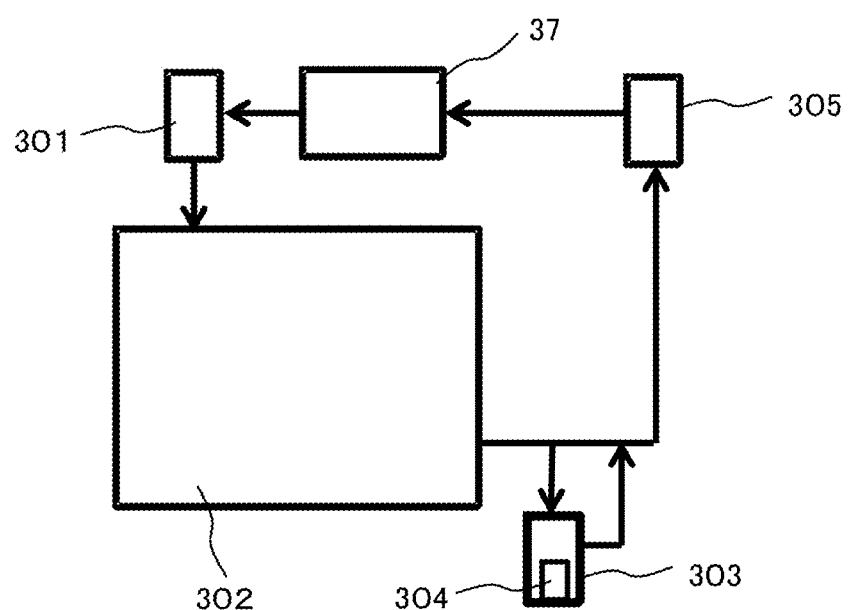
FIG. 9 is a conceptual diagram of a rotary component including a lubricant sensor.

FIG. 9 is a conceptual diagram of a rotary component including a lubricant sensor. The lubricant is supplied to a rotary component 302 from a lubricant supply device 301 such as a pump. The lubricant supply device 301 is connected to the oil tank 37 to receive a supply of the lubricant. The rotary component 302 is, for example, the gearbox 33 and other general portions where mechanical contact occurs, and is not particularly limited.

A sensor group 304 is disposed in a flow passage or the like of the lubricant to detect a state of the lubricant. In this example, a measurement unit 303 is provided in a flow passage (in the vicinity of an end of the lubricant passage) which branches off from a flow passage of the lubricant connected to an oil discharge port for the lubricant in the rotary component 302, and a part of the lubricant is introduced to the measurement unit 303. Then, the sensor group 304 is installed in the measurement unit 303. The reason that the measurement unit 303 is not provided in the main flow passage of the lubricant is to adjust the flow speed of the lubricant in the measurement unit 303 to a flow speed suitable for detecting a state of the lubricant. The lubricant discharged from the rotary component 302 returns to the oil tank 37 via a filter 305. Incidentally, the filter 305 is not indispensable.

The sensor group 304 measures various parameters of the lubricant. Examples of a physical quantity include temperature and oil pressure. The parameters can be measured, for example, using the known sensors disclosed in JP 2016-126007 A, WO 2010/150526 A, JP 2012-117951 A, JP 2012-181168 A, and JP 2016-044681 A. The state of the lubricant can be evaluated based on a change in the parameters over time. In this example, a sensor for temperature or the like is not indispensable; however, it is preferable that the sensor for temperature or the like is provided to detect a state of the lubricant in more detail. In addition, the sensor group 304 can include, for example, a sensor that measures information regarding contamination particles contained in the lubricant, for example, the concentration of the particles. The particles have the high possibility of resulting from the wear of components; and thereby, it is possible to detect the deterioration of the lubricant or an abnormality of the apparatus. An abnormality detected by a sensor that measures contamination particles has the possibility of being an abnormality that has already started; however, since it is possible to acquire information of the sensor in real time, it is useful to monitor contamination particles.

In a large rotary component of the wind turbine or the like, the sensor group 304 may be installed not in a flow passage but in a lubricant storage portion of a bottom portion of the rotary component 302.

Then, in this example, the sensor group 304 includes an optical sensor including a visible light source and a photodetector. The optical sensor measures light, which is transmitted through the lubricant, to acquire chromaticity information (values of R, G, and B) of the lubricant. The diagnosis of the deterioration level and the diagnosis of the residual life are performed based on the acquired chromaticity data. In a diagnosis based on sensor data, the diagnosis is performed based on sensor data from the optical sensor or sensor data from the optical sensor and one or a plurality of types of other sensors.

The quality of the lubricant deteriorates with use, and the lubricant does not carry out the initial function. For this reason, it is necessary to perform maintenance such as replacement according to deterioration situations of the quality. It is useful in terms of the efficiency of maintenance management that data collectable by the sensor group 304 which is installed at the actual site to know the timing of such a maintenance can be monitored at a remote site. For example, the data collected by the sensor group 304 is collected by the server 210 inside the nacelle 3, and thereafter, the data is transmitted to the central server 240, which aggregates data of a plurality of the farms, via the aggregation server 220 that aggregates data in the farm 200.

In addition, the aggregated data may include not only data regarding the lubricant but also data indicating the operating conditions of the wind power generator. Examples of the data indicating the operating conditions include the output value of the wind turbine (the larger the output value is, the larger the speed of deterioration of the lubricant is), the actual operation time (the longer the actual operation time is, the larger the speed of deterioration of the lubricant is), the temperature of the machine (the higher the temperature is, the larger the speed of deterioration of the lubricant is), and the rotation speed of the shaft (the higher the rotation speed is, the larger the speed of deterioration of the lubricant is). The foregoing data can be collected from the sensors with the known configurations installed at places of the wind power generator, or control signals of the devices.

(3. Flow of Diagnosis of Lubricant)

Figure 10:
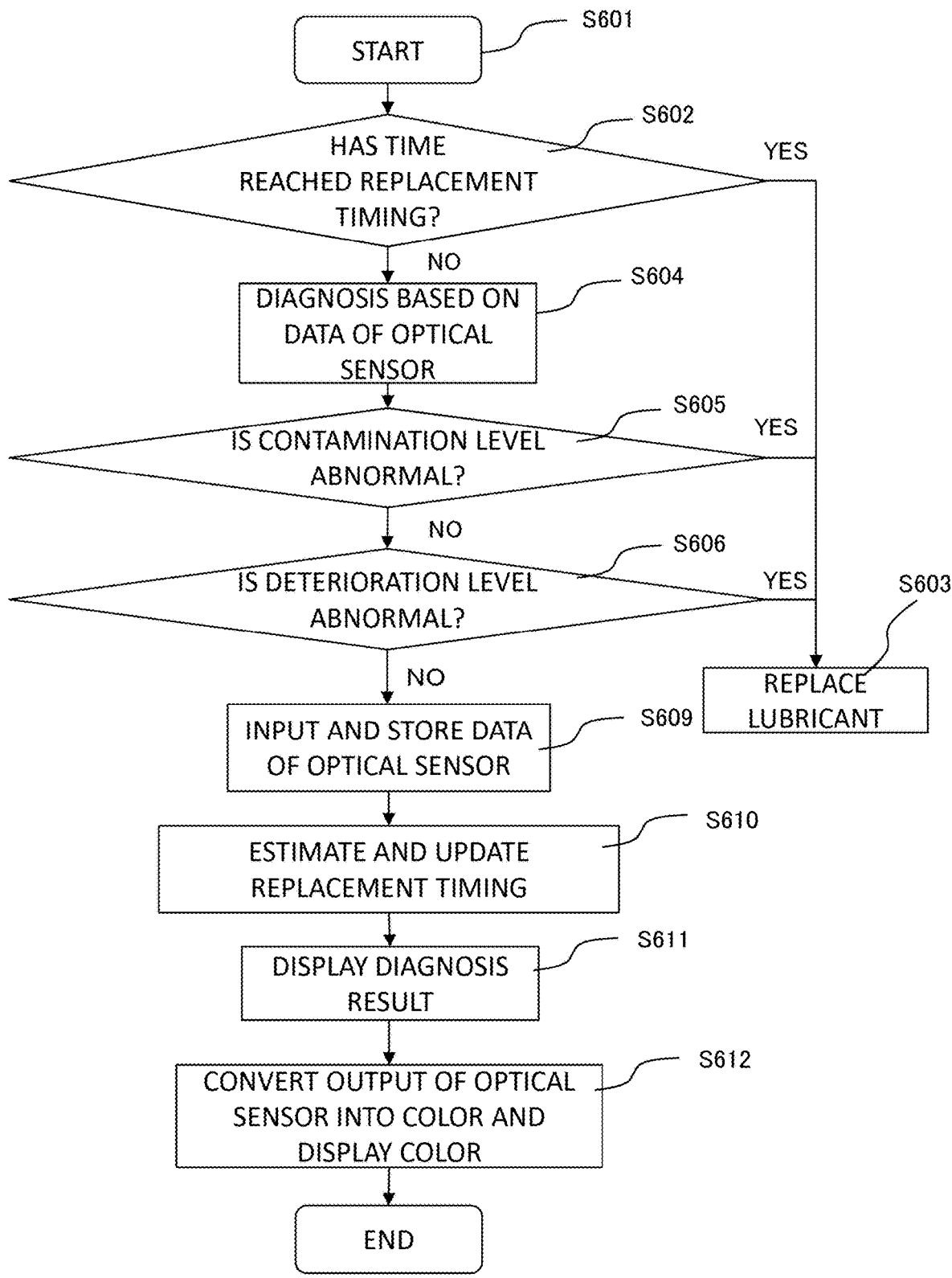
FIG. 10 is a flowchart for diagnosing the lubricant.

FIG. 10 is a flowchart illustrating a process of diagnosing the lubricant in this example. The process illustrated in FIG. 10 is performed under the control of any one of the server 210, the aggregation server 220, and the central server 240 in FIG. 8. In the following example, the central server 240 performs the process. A processor executes software stored in the storage device of the server to perform determined processes in conjunction with other hardware, so that functions such as calculation and control are realized. Incidentally, a function equivalent to a function configured in software can be realized by hardware such as a field programmable gate array (FPGA) or an application specific integrated circuit (ASIC).

When the central server 240 performs control, since the central server 240 includes the plurality of wind power generators 1 thereunder, the following process is performed in each of the wind power generators. This process is basically a repetitive process, the start timing is set by a timer or the like, and for example, the process starts at 0 o'clock every day (S601). In addition, the central server 240 can perform the process at a random timing according to an instruction of an operator.

In a step S602, the central server 240 checks the replacement timing of the lubricant. The initial value of the replacement timing can be physically calculated using the Arrhenius reaction rate, for example, on the assumption that the lubricant operates at a design temperature, so that the residual life can be initially set. Such a calculation method is described, for example in JP 2016-044681 A. The replacement timing can be updated later based on measured data in a step S610.

When the replacement timing of the lubricant is reached, the replacement of the lubricant is performed in a step S603. Since the replacement of the lubricant is usually performed by a worker, the central server 240 performs a display or a notification to instruct the worker on the time and the target where a replacement has to be performed.

When the replacement timing of the lubricant is not reached, in a step S604, the central server 240 performs a diagnosis based on sensor data. In addition to chromaticity information of the lubricant obtained by the optical sensor, temperature, oil pressure, the concentration of particles contained in the lubricant, and the like can be used as the sensor data. The data collected by the sensor group 304 is transmitted to the central server 240, and for example, the central server evaluates the properties of the lubricant by comparing the parameters obtained from the sensors to the threshold values determined in advance.

When diagnostic results in steps S605 and S606 are abnormal, the replacement of the lubricant is performed in the step S603. When there is no abnormality, a step S609 is performed. In the step S605, the relative contamination level is measured based on the principle described with reference to FIGS. 2 to 7. In addition, for example, another algorithm or the like, which determines that the contamination level is abnormal when all the values of R, G, and B of the optical sensor are lower than predetermined threshold values, may be added.

In the step S606, when the deterioration level which is obtained from the chromaticity measured by the optical sensor using the correlation between the deterioration level and the chromaticity based on the principle described with reference to FIG. 4B exceeds a predetermined threshold value, it is determined that the deterioration level is abnormal. Incidentally, since the deterioration level is related to the concentration of the additive that is represented by the extreme-pressure agent and contained in the lubricant, the concentration of the additive may be calculated from the deterioration level. In addition, instead of or in addition to the principle described with reference to FIG. 4B, based on the chromaticity coordinate of the lubricant which is a diagnosis target and the correlation obtained in advance, the concentration of the additive such as the extreme-pressure agent contained in the lubricant which is the diagnosis target may be quantified and the concentration of the additive and the predetermined threshold value may be compared to each other to determine the deterioration level.

In the step S609, chromaticity measurement data and the like are input to the central server 240, and the data is chronologically stored.

From the viewpoint of the preventive preservation and the scheduled maintenance of the wind power generator, it is desirable to perform a predictive diagnosis of a change in the properties of the lubricant based on a transition in the deterioration level or contamination level before it is determined that there is an abnormality. Then, for example, a diagnosis result is displayed on a monitor or the like of the central server 240 which the worker can see (S611). In this case, for example, as shown in FIGS. 2 to 4B, when the output of the optical sensor is converted into color information and the converted color information is displayed, it is easy to intuitively understand the deterioration level or the contamination level (S612). In addition, as shown in FIGS. 5 and 6, the data may be display in an aligned manner.

For example, on one occasion, the values of sensor data ($\Delta E$ and MCD) of the lubricant in the gearbox of the wind turbine are (380 and 10), and in this case, the distance to the deterioration curve 100, namely, the shift amount of the $\Delta E$ is 45. Since the contamination limit of the lubricant is 20, the relative contamination amount of the lubricant is 225%. Since the correlation factor between the contamination amount and the output of the wind turbine is 0.2 for ten hours immediately before the time the above sensor data is obtained, the contamination level of the lubricant is determined to be abnormal, and the sampling and analysis of the lubricant and the inspection of mechanical components are displayed and notified.

In another wind turbine, at another time, the values of sensor data (ΔE and MCD) of the lubricant in the gearbox of the wind turbine are (400 and 53), and in this case, the distance to the deterioration curve, namely, the shift amount of the ΔE is 3. Since the contamination limit of the lubricant is 18, the relative contamination amount of the lubricant is 17%. Since the relative contamination amount is less than 100%, the contamination level of the lubricant is determined to be normal without the evaluation of the correlation between the contamination level and the operation parameters, and a determination result is displayed and notified. Subsequently, the diagnosis of the residual life of the lubricant is performed to determine that the lubricant has a limit life of five years, a relative deterioration level of 30%, and a residual life of three and a half years, and a determination result is displayed and notified.

As described above, in this example, the severity of the contamination level in the lubricant becomes known using the sensor data of the lubricant and the output behaviors of the wind turbine; and thereby, it is possible to correctly detect an abnormality of the lubricant at an early stage. For this reason, an abnormality of the wind power generator can be prevented beforehand by an appropriate maintenance such as the replacement of the lubricant. In addition, it is also possible to optimize the replacement period of the lubricant.

When the optical sensor is installed inside the nacelle, the contamination and the deterioration of the lubricant can be remotely monitored on-line.

In this example, the method and the system where the optical sensor is installed in the lubricant of the rotary component to monitor the lubricant have been described; however, the same diagnosis can be performed by sampling the lubricant from the rotary component at the time of inspection or the like, and performing measurement using an optical sensor outside the rotary component.

SECOND EXAMPLE

In a second example, the estimation of the life of the lubricant is corrected using data obtained from the sensors. In the first example, it is assumed that the operating conditions of the wind power generator 1 are constant and unchanged. However, actually, the operating conditions of the wind power generator 1 are not constant, and the conditions change due to various factors.

For example, artificial changes in the operating conditions include the downtime period of the apparatus for inspection and an operation adjustment to adjust the power generation amount. The change parameters can be acquired as operation parameters of the wind power generator 1.

In addition, the factors of change in the operating conditions which result from the natural world include weather including wind speed, temperature, humidity, and the like which are factors inside and outside the wind power generator. The factors of change in the operating conditions can be measured by various sensors. Therefore, it is possible to more accurately determine and predict the state of the lubricant by reflecting the foregoing factors of change as sensor data.

As described with reference to FIGS. 8 and 9, various sensors can be installed in the wind power generator. The sensor data from the sensor group 304 is transmitted to the aggregation server 220 or the central server 240 via the server 210. In addition, the operation parameters of the wind power generator 1 can be obtained from the server 210, the aggregation server 220, or the central server 240 which performs the control.

Referring again to FIG. 10, a method for monitoring the lubricant which reflects the operating conditions will be described. The basic process is the same as that described with reference to FIG. 10; however, in a diagnosis process using sensor data (S604), the sensor data or the operation parameters are chronologically stored and used in a replacement timing estimation and update process (S610).

In order to simplify the description, in this example, a mechanism for supplying the lubricant to a bearing portion is set as a target, and a parameter for controlling the number of revolutions R (rpm) of the shaft is used as an operation parameter indicating the operating condition. The sensor data or the operation parameter is not limited thereto, and other various sensor data or operation parameters can be used. In this example, data of the various sensors is aggregated to the central server 240 and is collectively processed here; however, the present invention is not limited thereto.

In the replacement timing estimation and update process (S610), the central server 240 acquires a result of measurement of the relative contamination level which is input in the step S609, and the parameter for controlling the number of revolutions R of the shaft which is stored in the step S604. The foregoing data is chronologically stored together with time data in the storage device.

Now, as a simple example, it is assumed that the number of revolutions R (rpm) of the shaft is related to an increase in the relative contamination level. Since, under this assumption, a relative contamination level $C(t)$ can be identified as a function of a time t and the number of revolutions R of the shaft, $f(t, R)=C(t)$. The function $f(t, R)$ can be modeled by experiment or simulation, or based on the past data of t, R, and the relative contamination level. Therefore, when the prediction of the future value of $C(t)$ is performed in the replacement timing estimation and update process (S610), a change in the number of revolutions R of the shaft is reflected. The result is displayed, for example, in a display device of the central server 240.

FIG. 11 is a graph showing an example where a future value 1002 is predicted based on past one-year data 1001 of the wind power generator 1 and displayed. Past one-year data 1003 is a measured value. Future data 1004A and 1004B are predicted values.

Figure 11A:
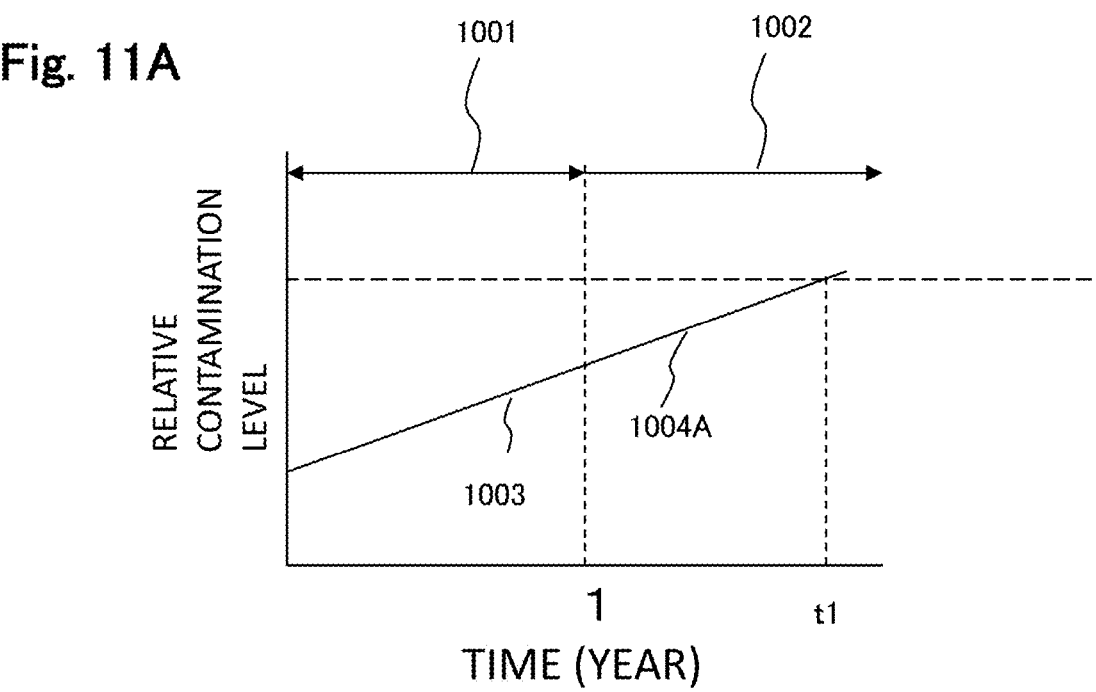
FIGS. 11A and 11B is a graph showing a concept of estimating the residual life of the lubricant.

In FIG. 11A, the future operating condition does not change, and the number of revolutions R is always constant. In this case, the future value (predicted data) 1002 of the relative contamination level makes a transition similar to the past one-year data 1001. In this case, the limit of the relative contamination level is predicted when a time t1 is reached.

Figure 11B:
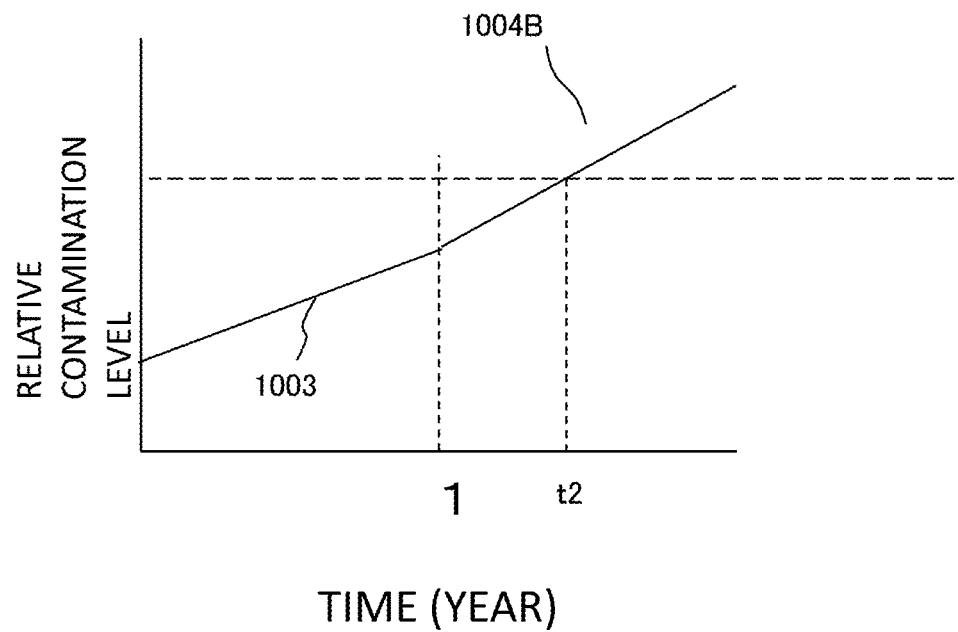

In FIG. 11B, the future operating condition changes, and the number of revolutions R after the elapse of one year is larger than that in the past one year. Here, when the degree of increase in the relative contamination level is proportional to the number of revolutions R, the predicted data of the relative contamination level does not make a transition similar to that in the past one year, but for example, as shown by 1004B in FIG. 11B, the ratio of increase becomes large. In this case, the limit of the relative contamination level is predicted when a time t2 earlier than t1 is reached.

In the above description, the degree of increase in the relative contamination level is corrected using the number of revolutions R of the shaft as the operation parameter; however, the sensor data can be also used. For example, it is considered that the mixing in of moisture is related to the relative contamination level. Under this assumption, the relative contamination level C(t) can be identified as a function of the time t and a humidity T, and the relative contamination level can be corrected in the same manner as in the case of the number of revolutions R of the shaft.

As in the example shown in FIG. 11, it is possible to more accurately determine the timing the parameter indicating the contamination level exceeds the threshold value by reflecting the operation parameter representing the operating condition of the wind power generator or the sensor data in the predicted data. Namely, it is possible to more accurately determine a future relative contamination level based on a past relative contamination level, a past operation parameter (or sensor data), and a future operation parameter (or predicted sensor data).

Future data of a parameter such as an operation time or a target power generation value, which can be artificially controlled among the parameters representing the operating conditions, can be prepared according to an operation schedule and the like. For this reason, it is possible to increase the accuracy of prediction by using the parameter representing the operating condition in predicting the deterioration of the lubricant.

In addition, future data of a parameter such as weather or temperature which cannot be artificially controlled can be predicted from past record data. For this reason, similarly, it is possible to increase the accuracy of prediction by using the parameter representing the operating condition in predicting the deterioration of the lubricant.

Figure 12:
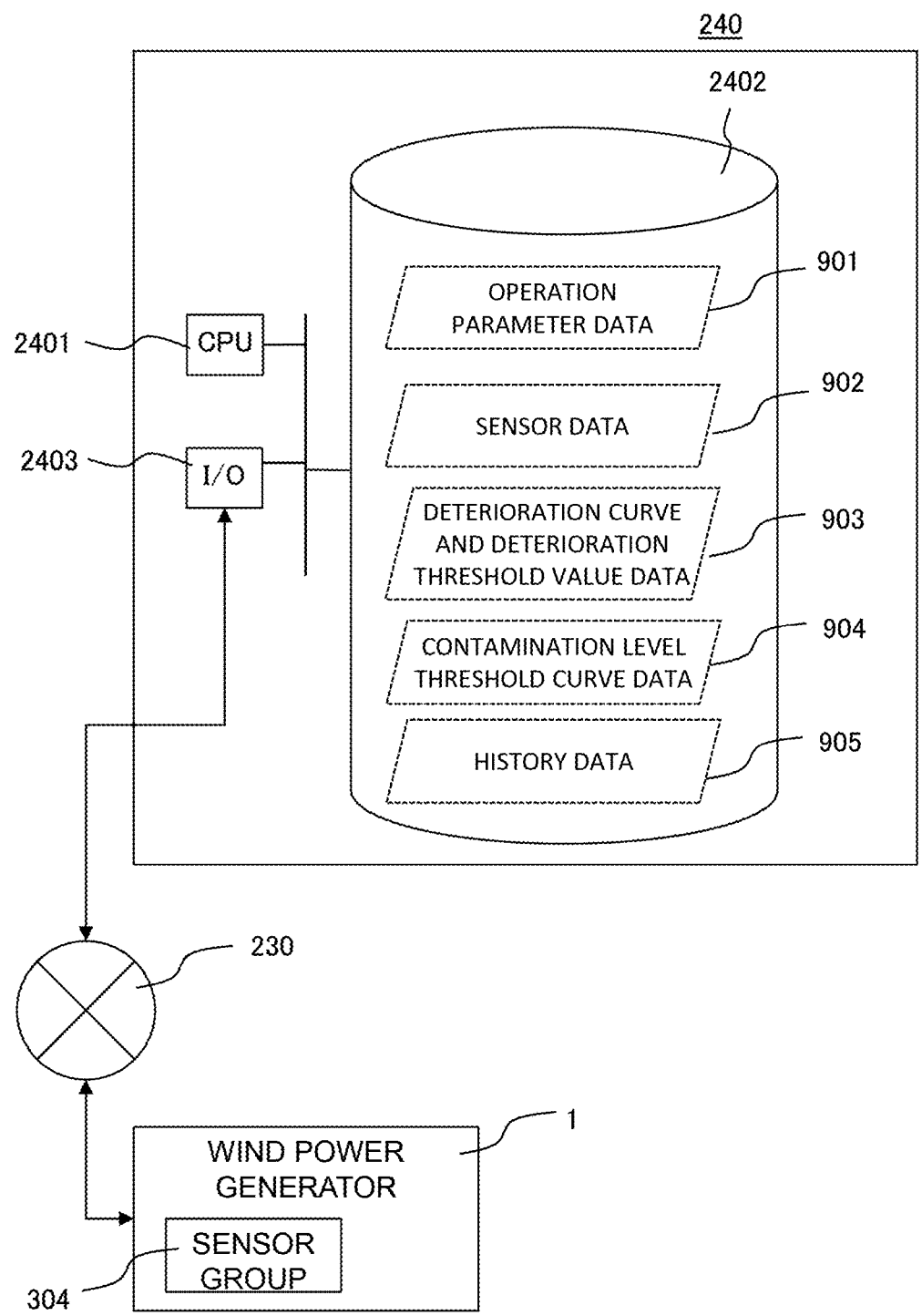
FIG. 12 is a block diagram illustrating an example of a central server in another example.

FIG. 12 is a block diagram illustrating an example of the configuration of the central server 240 in this example. The central server 240 includes a processing device 2401, a storage device 2402 (a magnetic disk device, a semiconductor memory, or the like), and an input and output device 2403 which are basic server configurations. The input and output device 2403 includes an input device such as a general keyboard or a general mouse and an output device such as an image display device or a printer. In addition, the input and output device 2403 includes a network interface that exchanges data with the wind power generator 1, the server 210 of the wind power generator 1, the aggregation server 220, or an additive quantitative analysis system (not illustrated) such as a liquid chromatograph mass spectrometer via the network 230.

Various operation parameters or sensor data are input to the central server 240 from the wind power generator 1 and the sensor group 304 of the wind power generator 1 directly or via the server 210 or the aggregation server 220. Alternatively, the operation parameters or the sensor data may be input to the central server 240 via a portable recording medium instead of via a network. The foregoing data is stored in the storage device 2402 as chronological operation parameter data 901 or chronological sensor data 902. In this example, as one sensor of the sensor group 304, for example, a transmission optical sensor which includes a visible light source and a photodetector to measure the chromaticity of the lubricant is used. The relative contamination level or the relative deterioration level in the lubricant is quantified by the chromaticity of the lubricant obtained by the optical sensor. For this reason, the sensor data 902 chronologically stores chromaticity data of the lubricant or the values of the ΔE and the MCD, which are calculated from the chromaticity data, in addition to the chromaticity data.

Since the relative contamination level or the relative deterioration level is calculated from the values of the ΔE and the MCD, deterioration curve and deterioration threshold value data 903 are stored in the storage device 2402. The deterioration curve data is indicated by the deterioration curve 100 in FIGS. 2 to FIG. 4B. The deterioration threshold value data is indicated by the deterioration threshold value 402 in FIG. 4B.

In addition, contamination level threshold curve data 904 is stored in the storage device 2402. The contamination level threshold curve data 904 is indicated by the contamination level threshold curve 401 in FIG. 4B. The processing device 2401 calculates the relative contamination level and the relative deterioration level from the sensor data 902 using the deterioration curve and the deterioration threshold value data 903 and the contamination level threshold curve data 904. The relative contamination level and the relative deterioration level are stored as history data 905 in the storage device 2402.

The processing device 2401 predicts the speed of deterioration of the lubricant using the history data 905 and, as needed, the operation parameter data 901 and the sensor data 902 which are stored in the storage device 2402, and outputs the predicted speed of deterioration to the output device. When the relative contamination level is used as an index, in this example, it is possible to more accurately determine the timing a parameter indicating the quality of the lubricant such as the relative contamination level exceeds a threshold value by reflecting the operation parameter representing the operating condition or the sensor data.

In the example described with reference to FIG. 11, the relative contamination level is corrected by the operation parameter representing the operating condition or the like; however, the horizontal axis may represent the total number of revolutions of the generator which is information on the operation of the wind turbine or the total power generation amount instead of the elapsed period. Also in this example, it is possible to more accurately determine the timing the relative contamination level exceeds the threshold value.

As described above, in this example, the relative contamination level is measured to properly monitor the lubricant that is used in the important rotary components (bearings) such as the main shaft, the generator, the yaw bearing, and the pitch bearing, or the gearbox in the wind power generator. In addition, a sensor is installed in the vicinity of an oil discharge port of a rotary component provided in an automatic lubricant supply mechanism, so that monitoring (on-line monitoring) can be steadily performed. In addition, it is possible to perform a more accurate predictive diagnosis by monitoring parameters of the operating conditions of the wind power generator; and thereby, it is possible to early predict the replacement timing of the lubricant. As a result, the downtime of the wind power generator is shortened, and thus maintenance costs are reduced and the power generation amount is improved.

Incidentally, the present invention is not limited to the foregoing examples, and includes various modification examples.

For example, the foregoing examples have been described in detail so as to describe the present invention in an easy-to-understand manner, and the present invention is not necessarily limited to including the described entire configuration. In addition, a part of the configuration of an example can be replaced with the configuration of another example, and the configuration of another example can be added to the configuration of an example. In addition, another configuration can be added to, removed from, or replaced with a part of the configuration of each example.

For example, in the foregoing examples, the wind power generator has been described as the rotary machine; however, the present invention is also applicable to diagnosing the deterioration of a lubricant of rotary machines (an engine, a turbine, a speed reducer, and the like) of a nuclear power generator, a thermal power generator, and a ship, and rotary machines such as a geared motor, a wheel flange of a railway vehicle, a compressor, a transformer, a movable plant machine, and a large pump machine.

In addition to an extreme-pressure agent, the consumption of an additive such as an anti-wear agent, an oiliness agent, an anti-corrosive agent, or a defoamer is applicable to the diagnosis as an index of the deterioration of the lubricant.

THIRD EXAMPLE

In the first example, the deterioration curve 100 or the contamination level threshold curve 401 is linearly approximated, and can be expressed by $y=-\Delta x+B$. On the other hand, the deterioration curve is not limited to a straight line, and can be represented by a proper curve from experiments on the deterioration of the lubricant.

Figure 13:
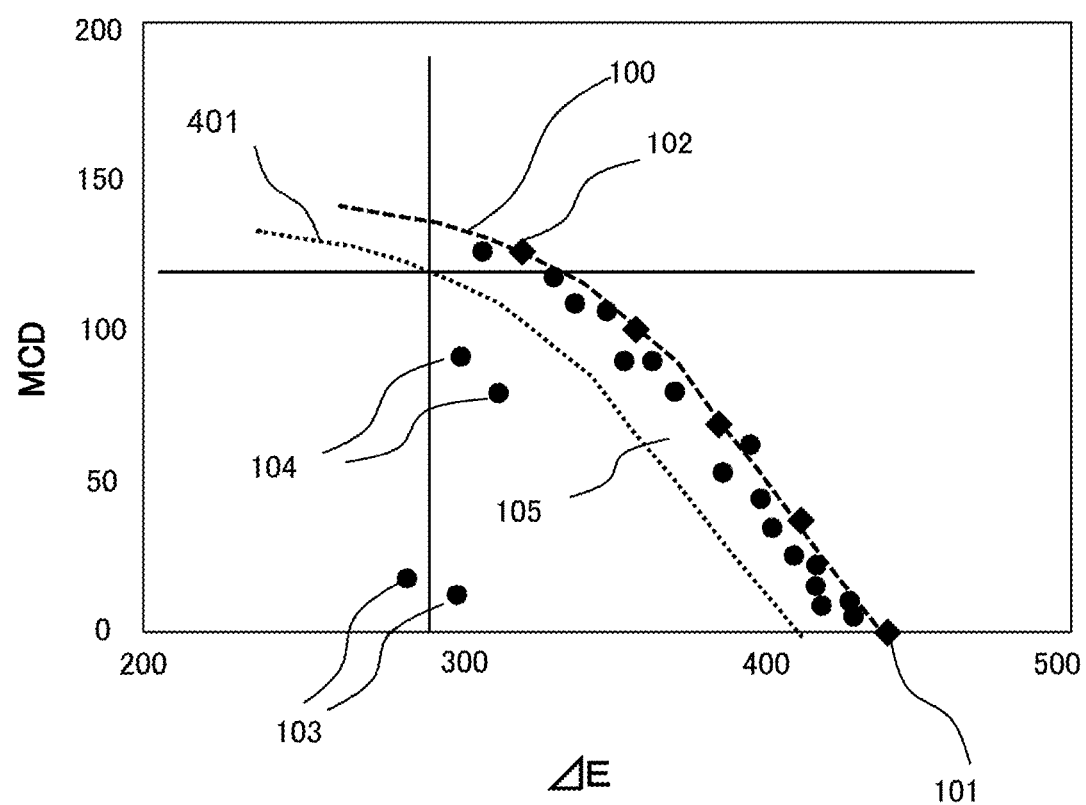
FIG. 13 is a graph showing a deterioration curve and a distribution of normal and abnormal samples.

As shown in FIG. 13, as the deterioration of the lubricant makes progress, the deterioration curve 100 or the contamination level threshold curve 401 may not be a straight line. Also in this case, due to the contamination of the lubricant, the plots of samples are shifted to a direction where the $\Delta E$ decreases. A region between the deterioration curve 100 and the contamination level threshold curve 401 is the normal range 105. In addition, 103 denotes a sample contaminated by water, 104 denotes a sample contaminated by solid particles, and both are samples of which the contamination exceeds a reference value (threshold value).

Figure 14:
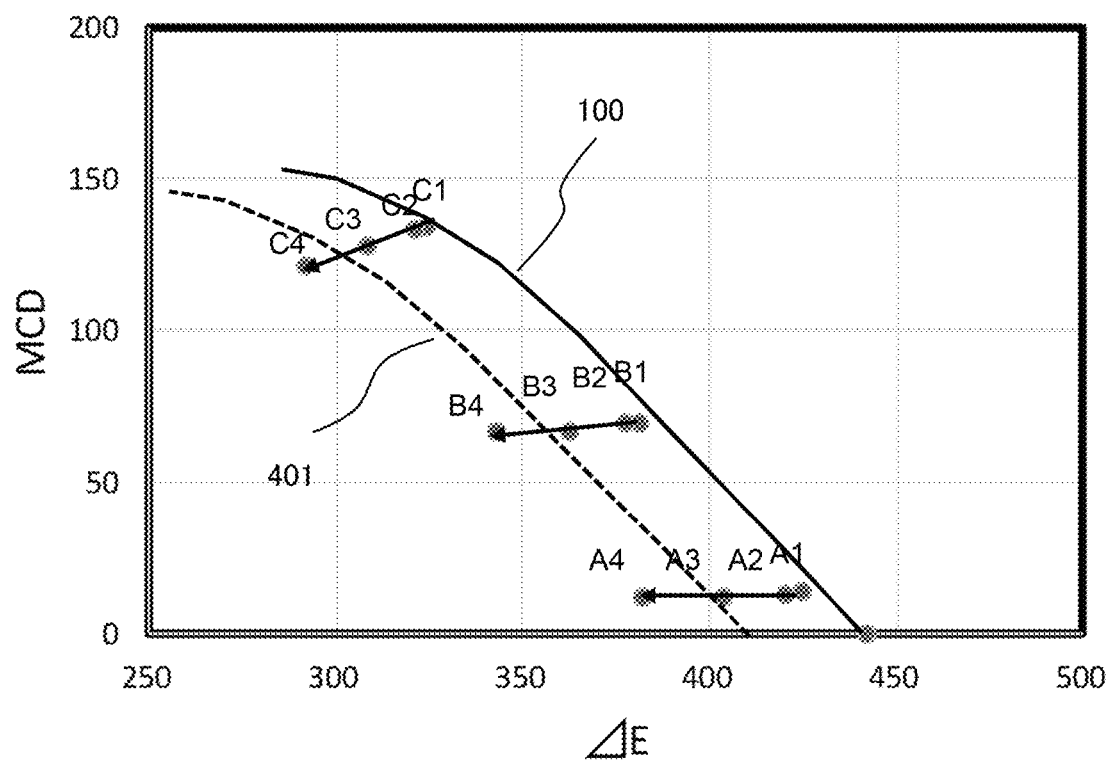
FIG. 14 is a graph showing a result of calculation of a shift of plots caused by the contamination of the lubricant.

FIG. 14 shows changes in the scores of the $\Delta E$ and the MCD caused by the contamination of the lubricant. Compared to the transmittance of a lubricant sample X1 (X is A, B, or C), due to contamination, the transmittance of X2 (X is A, B, or C) is decreased by 1%, the transmittance of X3 (X is A, B, or C) is decreased by 5%, and the transmittance of X4 (X is A, B, or C) is decreased by 10%. When the relative contamination level of a sample C of which the contamination has made progress is obtained, it is preferable to calculate the relative contamination level using a straight line (contamination curve) connecting C1 and C4. For example, when C1 is a sample that is not contaminated, the relative contamination level of a sample C4 is (distance from C1 to C4)/(distance from C1 to the contamination level threshold curve 401)×100.

When it is not desirable to approximate the contamination curve to a straight line, instead of the straight line shown in FIG. 14, a curve may be used. In that case, in order to indicate the distance, a distance (length) along the curve may be used instead of a straight line (shortest distance).

Figure 15:
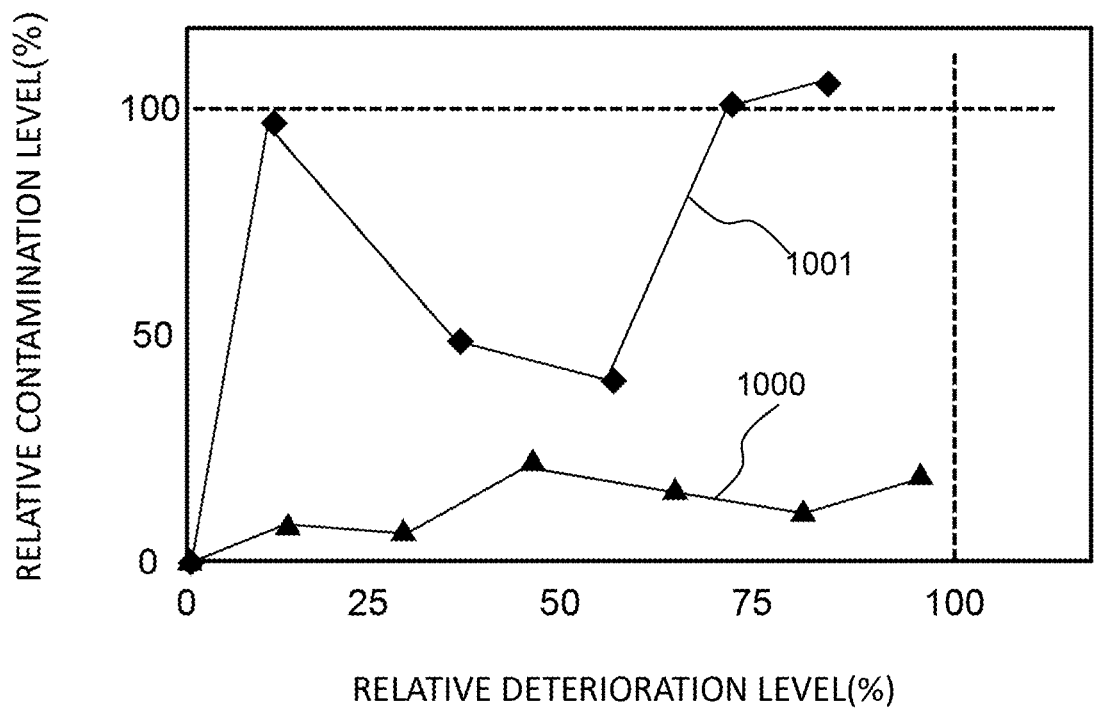
FIG. 15 is a graph showing a relationship between a relative deterioration level and a relative contamination level.

FIG. 15 is a graph showing transitions over time in the relative deterioration level and the relative contamination level of a lubricant of a gearbox of each of a wind turbine A 1000 with a capacity of 5 MW and a wind turbine B 1001 with a capacity of 5 MW every half year. Two wind turbines continuously operate except for being in a periodic inspection period. When three and a half years have elapsed, the relative deterioration level of the wind turbine A 1000 exceeds 90%, and thus it is determined that the lubricant is replaced when four years have elapsed. When a half year has elapsed, the relative contamination level of the wind turbine B 1001 exceeds 90%; however, since a transition in the relative contamination level synchronizes with the transition in the output of the wind turbine immediately therebefore and immediately thereafter, and the relative contamination level decreases within the reference value when one year has elapsed, thereafter, the progression is observed. Thereafter, when two years have elapsed, the relative contamination level reaches 100%, thereafter, the relative contamination level does not synchronize with the transition in the output of the wind turbine, and when two and a half years have elapsed, the relative contamination level increases further, and thus it is determined that the lubricant is replaced when three years have elapsed.

As described above, in this example, since the deterioration curve obtained in advance and a limit contamination curve obtained using a contaminated sample (a sample containing water or the like) are used, and the contamination level of the sample is obtained using the distance from the deterioration curve and the distance from the limit contamination curve, both of the deterioration level and the contamination level of the lubricant can be evaluated by one chromaticity sensor. In addition, in the description of the example, the chromaticity sensor is provided inside the wind turbine; however, even when the lubricant is sampled and taken out from the wind turbine, and a measurement is performed outside the wind turbine, the same effects are obtained.

According to the technique disclosed in the examples, it is possible to obtain the concentration of the additive of the lubricant using chromaticity data obtained based on measurement data of the optical sensor, and diagnose the deterioration of the lubricant based on the obtained concentration. In addition, the system of monitoring the lubricant includes the optical sensor, the input device, the processing device, the storage device, and the output device. The storage device can chronologically store the concentration of the additive of the lubricant which is obtained by the optical sensor, and based on the additive concentration data, the processing device can estimate the time the concentration of the additive reaches the predetermined threshold value.

In addition, in the foregoing examples, even when a part of wear powder is trapped by the oil filter provided in the large machine or the wear powder increases due to a change or the like in the load of the machine, and thus the contamination level of the lubricant due to solid powder changes, the contamination can be diagnosed. In addition, when both of the contamination and the deterioration of the lubricant can be diagnosed by the optical oil sensor, the knowledge about the order of diagnosis of the contamination level and the deterioration level is as described above.

What is claimed is:

1. A method for diagnosing a lubricant containing an additive, which is executed by an information processing apparatus including an input device, a processing device, a storage device, and an output device, the method comprising:

a diagnosis of a deterioration; and
   a diagnosis of a contamination,
   wherein chromaticity information of the lubricant which is a diagnosis target is obtained from the input device, the chromaticity information being obtained by an optical sensor,
   the storage device stores a deterioration curve of the lubricant which is the diagnosis target, the deterioration curve being determined in advance regarding a transition in a chromaticity coordinate caused by a deterioration, and a chromaticity coordinate corresponding to a limit contamination level determined in advance using a contaminated lubricant, and
   in the diagnosis of the contamination of the lubricant, the processing device obtains a chromaticity coordinate of the lubricant, which is the diagnosis target, from the chromaticity information, and uses a relative contamination level which is obtained from a distance of the chromaticity coordinate of the lubricant, which is the diagnosis target, from the deterioration curve and a distance of the chromaticity coordinate corresponding to the limit contamination level from the deterioration curve, wherein the obtained chromaticity coordinate of the lubricant is compared to a threshold value for a contamination level of the lubricant on the chromaticity coordinate to determine the contamination, wherein the chromaticity coordinate is a two-dimensional coordinate based on a difference between a maximum value and a minimum value among R, G, and B color coordinates (MCD) and a color difference ($\Delta E$), and wherein the relative contamination level is derived based on a positional relationship between the deterioration curve and the contamination level threshold curve and a positional relationship between the deterioration curve and the position of the chromaticity information of the lubricant which is the diagnosis target on the chromaticity coordinate.

2. The method for diagnosing a lubricant according to claim 1, wherein in the diagnosis of the deterioration of the lubricant, a concentration of the additive contained in the lubricant which is the diagnosis target is quantified based on the chromaticity coordinate of the lubricant which is the diagnosis target, and a correlation obtained in advance, and the diagnosis of the contamination is performed before the diagnosis of the deterioration.

3. The method for diagnosing a lubricant according to claim 1, wherein in the diagnosis of the deterioration of the lubricant, a chromaticity coordinate of a limit deterioration level is determined in advance with respect to the deterioration curve, and a relative deterioration level, which is obtained from the chromaticity coordinate of the lubricant which is the diagnosis target and the chromaticity coordinate of the limit deterioration level, is used.

4. The method for diagnosing a lubricant according to claim 1, wherein the lubricant which is the diagnosis target is a lubricant that is used in a gearbox of a wind turbine, and when a state where the relative contamination level of the lubricant which is the diagnosis target is one or greater continues for a predetermined period, and a correlation factor between a transition in the relative contamination level for the predetermined period and a transition in an output of the wind turbine is below a correlation factor determined in advance, it is diagnosed that the lubricant which is the diagnosis target is in an abnormal contamination state, and a diagnosis result is notified by the output device.

5. The method for diagnosing a lubricant according to claim 1, wherein the chromaticity coordinate of the lubricant which is the diagnosis target, the chromaticity coordinate being obtained by measurement using the optical sensor, is a chromaticity coordinate in an RGB coordinate system.

6. A system of monitoring a lubricant that is supplied to a drive unit of a rotary machine, the system comprising:

an optical sensor that measures data regarding a chromaticity of the lubricant;
an input device;
a processing device;
a storage device; and
an output device, wherein the processing device quantifies a contamination level and a deterioration level of the lubricant which is a monitoring target based on a relationship, which is obtained in advance, between a concentration of an additive contained in a lubricant having a different degree of deterioration and a chromaticity coordinate of the lubricant having the different degree of deterioration, the chromaticity coordinate being obtained by the optical sensor, and a deterioration curve of the lubricant which is the monitoring target and wherein the processing device compares the obtained chromaticity coordinate of the lubricant to a threshold value for a contamination level of the lubricant on the chromaticity coordinate to determine the contamination, wherein the storage device holds data of the deterioration curve which indicates a transition in the chromaticity of the lubricant on a chromaticity coordinate as the lubricant deteriorates, and holds data of a contamination level threshold curve which indicates a threshold value for a contamination level of the lubricant on the chromaticity coordinate by the chromaticity of the lubricant, and the processing device calculates a relative contamination level of the lubricant which is the monitoring target based on a positional relationship on the chromaticity coordinate between the data regarding the chromaticity of the lubricant and the data of the deterioration curve, and a positional relationship on the chromaticity coordinate between the data of the contamination level threshold curve and the data of the deterioration curve.

7. A method for diagnosing a lubricant, which is executed by an information processing apparatus including an input device, a processing device, a storage device, and an output device, the method comprising:

preparing data of a deterioration curve which indicates a transition in a chromaticity of the lubricant on a chromaticity coordinate as the lubricant deteriorates;

preparing data of a contamination level threshold curve which indicates a threshold value for a contamination level of the lubricant on the chromaticity coordinate by the chromaticity of the lubricant;

obtaining chromaticity information of the lubricant which is a diagnosis target to specify a position on the chromaticity coordinate, the chromaticity information being optically measured; and deriving a relative contamination level of the lubricant from a positional relationship between the position of the chromaticity information of the lubricant which is the diagnosis target on the chromaticity coordinate, the deterioration curve, and the contamination level threshold curve wherein the relative contamination level of the lubricant is compared to the contamination level threshold curve to determine the contamination, wherein the chromaticity coordinate is a two-dimensional coordinate based on a difference between a maximum value and a minimum value among R, G, and B color coordinates (MCD) and a color difference ($\Delta E$), and wherein the relative contamination level is derived based on a positional relationship between the deterioration curve and the contamination level threshold curve and a positional relationship between the deterioration curve and the position of the chromaticity information of the lubricant which is the diagnosis target on the chromaticity coordinate.

8. The method for diagnosing a lubricant according to claim 7,
wherein a distance is used as the positional relationship.

9. The method for diagnosing a lubricant according to claim 8,
wherein the distance is a distance in a $\Delta E$ axis direction.

10. The method for diagnosing a lubricant according to claim 7,
wherein the contamination level threshold curve is positioned closer to a side, on which the $\Delta E$ is small, than the deterioration curve.

11. The method for diagnosing a lubricant according to claim 7,
wherein the data of the deterioration curve is prepared by optically measuring a sample that is obtained by performing a test on the lubricant, the test being performed under the same reaction condition and with only a reaction time changed.

12. The method for diagnosing a lubricant according to claim 7,
wherein the data of the contamination level threshold curve is prepared by optically measuring a plurality of samples having different deterioration levels and different contamination levels.

* * * * *